(12) United States Patent
Shelton, IV et al.

(10) Patent No.: US 10,835,310 B2
(45) Date of Patent: Nov. 17, 2020

(54) ELECTRICALLY-POWERED SURGICAL SYSTEMS

(71) Applicant: Ethicon LLC, Guaynabo, PR (US)

(72) Inventors: Frederick E. Shelton, IV, Hillsboro, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 578 days.

(21) Appl. No.: 15/689,628

(22) Filed: Aug. 29, 2017

(65) Prior Publication Data

US 2019/0059974 A1 Feb. 28, 2019

(51) Int. Cl.
*A61B 18/12* (2006.01)
*A61B 18/14* (2006.01)
(Continued)

(52) U.S. Cl.
CPC .......... *A61B 18/1447* (2013.01); *A61B 17/29* (2013.01); *A61B 17/320016* (2013.01); *A61B 18/1206* (2013.01); *A61B 18/14* (2013.01); *A61B 18/1442* (2013.01); *A61B 18/1445* (2013.01); *A61B 18/1482* (2013.01); *A61B 18/16* (2013.01); *A61B 34/30* (2016.02); *A61B 34/35* (2016.02); *A61B 17/07207* (2013.01); *A61B 17/10* (2013.01); *A61B 17/3201* (2013.01); *A61B 34/37* (2016.02); *A61B 34/74* (2016.02); *A61B 2017/00017* (2013.01); *A61B 2017/00022* (2013.01); *A61B 2017/00075* (2013.01); *A61B 2017/00221* (2013.01); *A61B 2017/00398* (2013.01); *A61B 2017/00818* (2013.01); *A61B 2017/07278* (2013.01); *A61B 2017/2936* (2013.01); *A61B 2017/2941* (2013.01); *A61B 2018/00184* (2013.01); *A61B 2018/00589* (2013.01); *A61B 2018/00595* (2013.01); *A61B 2018/00601* (2013.01);
(Continued)

(58) Field of Classification Search
CPC ...... A61B 18/14; A61B 18/1442–1447; A61B 18/1482; A61B 18/16; A61B 2018/1253; A61B 2018/1412; A61B 2018/146; A61B 34/30; A61B 34/35; A61B 34/37; A61B 34/74; A61B 2034/2051; A61B 2034/2059; A61B 2034/2065; A61B 2034/302; A61B 2034/305
See application file for complete search history.

(56) References Cited

U.S. PATENT DOCUMENTS 5,322,055 A 6/1994 Davison et al.
5,558,671 A 9/1996 Yates
(Continued)

FOREIGN PATENT DOCUMENTS

WO WO-2014151621 A1 9/2014
WO WO-2014151952 A1 9/2014

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — Daniel W Fowler
(74) *Attorney, Agent, or Firm* — Mintz Levin Cohn Ferris Glovsky and Popeo, P.C.

(57) ABSTRACT

Surgical systems and methods are provided for controlling actuation and movement of various surgical devices.

20 Claims, 23 Drawing Sheets

(51) Int. Cl.

| | | |
|---|---|---|
| *A61B 34/35* | (2016.01) | |
| *A61B 17/32* | (2006.01) | |
| *A61B 18/16* | (2006.01) | |
| *A61B 17/29* | (2006.01) | |
| *A61B 34/30* | (2016.01) | |
| *A61B 17/072* | (2006.01) | |
| *A61B 34/20* | (2016.01) | |
| *A61B 34/00* | (2016.01) | |
| *A61B 90/00* | (2016.01) | |
| *A61B 34/37* | (2016.01) | |
| *A61B 17/00* | (2006.01) | |
| *A61B 18/00* | (2006.01) | |
| *A61B 17/3201* | (2006.01) | |
| *A61B 17/10* | (2006.01) | |

(52) U.S. Cl.
CPC ........... *A61B 2018/00642* (2013.01); *A61B 2018/00678* (2013.01); *A61B 2018/00702* (2013.01); *A61B 2018/1253* (2013.01); *A61B 2018/146* (2013.01); *A61B 2018/1412* (2013.01); *A61B 2034/2051* (2016.02); *A61B 2034/2059* (2016.02); *A61B 2034/2065* (2016.02); *A61B 2034/302* (2016.02); *A61B 2034/305* (2016.02); *A61B 2090/031* (2016.02); *A61B 2090/036* (2016.02); *A61B 2090/062* (2016.02); *A61B 2090/064* (2016.02); *A61B 2090/065* (2016.02); *A61B 2090/066* (2016.02)

(56) References Cited

U.S. PATENT DOCUMENTS

| | | | |
|---|---|---|---|
| 5,792,135 | A | 8/1998 | Madhani et al. |
| 5,817,084 | A | 10/1998 | Jensen |
| 5,873,873 | A | 2/1999 | Smith et al. |
| 5,878,193 | A | 3/1999 | Wang et al. |
| 5,980,510 | A | 11/1999 | Tsonton et al. |
| 6,039,735 | A | 3/2000 | Greep |
| 6,066,137 | A | 5/2000 | Greep |
| 6,132,368 | A | 10/2000 | Cooper |
| 6,168,605 | B1 | 1/2001 | Measamer et al. |
| 6,231,565 | B1 | 5/2001 | Tovey et al. |
| 6,325,811 | B1 | 12/2001 | Messerly |
| 6,364,888 | B1 | 4/2002 | Niemeyer et al. |
| 6,500,176 | B1 | 12/2002 | Truckai et al. |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,380,696 | B2 | 6/2008 | Shelton, IV et al. |
| 7,381,209 | B2 | 6/2008 | Truckai et al. |
| 7,404,508 | B2 | 7/2008 | Smith et al. |
| 7,455,208 | B2 | 11/2008 | Wales et al. |
| 7,506,790 | B2 | 3/2009 | Shelton, IV |
| 7,524,320 | B2 | 4/2009 | Tierney et al. |
| 7,549,564 | B2 | 6/2009 | Boudreaux |
| 7,559,450 | B2 | 7/2009 | Wales et al. |
| 7,654,431 | B2 | 2/2010 | Hueil et al. |
| 7,691,098 | B2 | 4/2010 | Wallace et al. |
| 7,780,054 | B2 | 8/2010 | Wales |
| 7,784,662 | B2 | 8/2010 | Wales et al. |
| 7,798,386 | B2 | 9/2010 | Schall et al. |
| 7,806,891 | B2 | 10/2010 | Nowlin et al. |
| 7,824,401 | B2 | 11/2010 | Manzo et al. |
| 8,439,910 | B2 | 5/2013 | Greep et al. |
| 8,461,744 | B2 | 6/2013 | Wiener et al. |
| 8,469,252 | B2 | 6/2013 | Holcomb et al. |
| 8,602,286 | B2 | 12/2013 | Crainich et al. |
| 8,684,253 | B2 | 4/2014 | Giordano et al. |
| 8,771,270 | B2 | 7/2014 | Burbank |
| 8,986,302 | B2 | 3/2015 | Aldridge et al. |
| 9,023,071 | B2 | 5/2015 | Miller et al. |
| 9,072,536 | B2 | 7/2015 | Shelton, IV et al. |
| 9,095,367 | B2 | 8/2015 | Olson et al. |
| 9,119,657 | B2 | 9/2015 | Shelton, IV et al. |
| 9,168,092 | B2 | 10/2015 | Homer et al. |
| 9,393,037 | B2 | 7/2016 | Olson et al. |
| 9,445,816 | B2 | 9/2016 | Swayze et al. |
| 9,585,658 | B2 | 3/2017 | Shelton, IV |
| 9,713,468 | B2 | 7/2017 | Harris et al. |
| 9,713,471 | B2 | 7/2017 | Holcomb et al. |
| 2001/0003798 | A1 | 6/2001 | Mcgovern et al. |
| 2002/0077645 | A1 | 6/2002 | Wiener et al. |
| 2003/0040758 | A1 | 2/2003 | Wang et al. |
| 2003/0060927 | A1* | 3/2003 | Gerbi ............... A61B 34/71 700/245 |
| 2004/0167515 | A1 | 8/2004 | Petersen et al. |
| 2006/0079874 | A1 | 4/2006 | Faller et al. |
| 2007/0005055 | A1 | 1/2007 | Heim et al. |
| 2007/0191713 | A1 | 8/2007 | Eichmann et al. |
| 2007/0282333 | A1 | 12/2007 | Fortson et al. |
| 2008/0119870 | A1 | 5/2008 | Williams |
| 2008/0200940 | A1 | 8/2008 | Eichmann et al. |
| 2010/0042097 | A1* | 2/2010 | Newton ............ A61B 18/1445 606/41 |
| 2010/0168744 | A1* | 7/2010 | Sugiyama ........... A61B 1/0008 606/46 |
| 2010/0191282 | A1 | 7/2010 | Harris et al. |
| 2010/0198248 | A1 | 8/2010 | Vakharia |
| 2011/0015631 | A1 | 1/2011 | Wiener et al. |
| 2011/0087218 | A1 | 4/2011 | Boudreaux et al. |
| 2011/0087256 | A1 | 4/2011 | Wiener et al. |
| 2011/0295247 | A1 | 12/2011 | Schlesinger et al. |
| 2011/0295270 | A1 | 12/2011 | Giordano et al. |
| 2012/0078139 | A1 | 3/2012 | Aldridge et al. |
| 2012/0078243 | A1 | 3/2012 | Worrell et al. |
| 2012/0078247 | A1 | 3/2012 | Worrell et al. |
| 2012/0116379 | A1 | 5/2012 | Yates et al. |
| 2012/0292367 | A1 | 11/2012 | Morgan et al. |
| 2013/0012957 | A1 | 1/2013 | Shelton, IV et al. |
| 2013/0023868 | A1 | 1/2013 | Worrell et al. |
| 2013/0030428 | A1 | 1/2013 | Worrell et al. |
| 2013/0261648 | A1 | 10/2013 | Laurent et al. |
| 2013/0325034 | A1 | 12/2013 | Schena et al. |
| 2013/0331644 | A1* | 12/2013 | Pandya ............... B25J 9/1682 600/102 |
| 2014/0005718 | A1 | 1/2014 | Shelton, IV et al. |
| 2014/0142422 | A1 | 5/2014 | Manzke et al. |
| 2014/0151952 | A1 | 6/2014 | Kozaki |
| 2014/0166728 | A1 | 6/2014 | Swayze et al. |
| 2014/0171970 | A1 | 6/2014 | Martin et al. |
| 2014/0221738 | A1* | 8/2014 | Sholev ............... A61B 1/00149 600/102 |
| 2014/0263541 | A1 | 9/2014 | Leimbach et al. |
| 2014/0276931 | A1 | 9/2014 | Parihar et al. |
| 2015/0209059 | A1 | 7/2015 | Trees et al. |
| 2015/0209573 | A1 | 7/2015 | Hibner et al. |
| 2015/0272575 | A1 | 10/2015 | Leimbach et al. |
| 2015/0282825 | A1 | 10/2015 | Trees et al. |
| 2015/0365296 | A1 | 12/2015 | Bunte et al. |
| 2016/0019918 | A1 | 1/2016 | Juman |
| 2016/0019919 | A1 | 1/2016 | Gale et al. |
| 2016/0089175 | A1 | 3/2016 | Hibner et al. |
| 2016/0089533 | A1 | 3/2016 | Turner et al. |
| 2016/0175060 | A1 | 6/2016 | Park |
| 2016/0287252 | A1 | 10/2016 | Parihar |
| 2016/0367243 | A1 | 12/2016 | Martin et al. |
| 2017/0056038 | A1 | 3/2017 | Hess et al. |
| 2017/0196637 | A1 | 7/2017 | Shelton, IV et al. |
| 2017/0202609 | A1 | 7/2017 | Shelton, IV et al. |
| 2018/0000543 | A1 | 1/2018 | Hibner |
| 2018/0049813 | A1 | 2/2018 | Yates et al. |
| 2018/0214219 | A1 | 8/2018 | Overmyer et al. |

(56) References Cited

U.S. PATENT DOCUMENTS

2019/0038371 A1 2/2019 Wixey et al.
2019/0059973 A1 2/2019 Shelton, IV et al.
2019/0059991 A1 2/2019 Shelton, IV et al.

OTHER PUBLICATIONS

U.S. Appl. No. 15/237,653 entitled "Methods, Systems, and Devices for Controlling a Motor of a Robotic Surgical System" filed Aug. 16, 2016.
U.S. Appl. No. 15/422,767 entitled "Robotic Surgical System and Methods for Articulation Calibration" filed Feb. 2, 2017.
U.S. Appl. No. 15/634,620 entitled "Surgical Stapler with Independently Actuated Drivers to Provide Varying Staple Heights" filed Jun. 27, 2017.
U.S. Appl. No. 15/674,075 entitled "Clip Retention for Surgical Clip Applier" filed Aug. 10, 2017.
U.S. Appl. No. 15/674,086 entitled "Surgical Clip Applier Jaw Alignment" filed Aug. 10, 2017.
U.S. Appl. No. 15/674,096 entitled "Surgical Device with Overload Mechanism" filed Aug. 10, 2017.
U.S. Appl. No. 15/674,121 entitled "Jaw for Clip Applier" filed Aug. 10, 2017.
U.S. Appl. No. 15/674,125 entitled "Clip Appliers with Extended Jaw Tip" filed Aug. 10, 2017.
U.S. Appl. No. 15/674,166 entitled "Surgical Clip Applier" filed Aug. 10, 2017.
U.S. Appl. No. 15/689,072 entitled "Methods, Systems, and Devices for Controlling Electrosurgical Tools" filed Aug. 29, 2017.
U.S. Appl. No. 29/613,511 entitled "Clip Applier Rotation Knob" filed Aug. 10, 2017.

\* cited by examiner

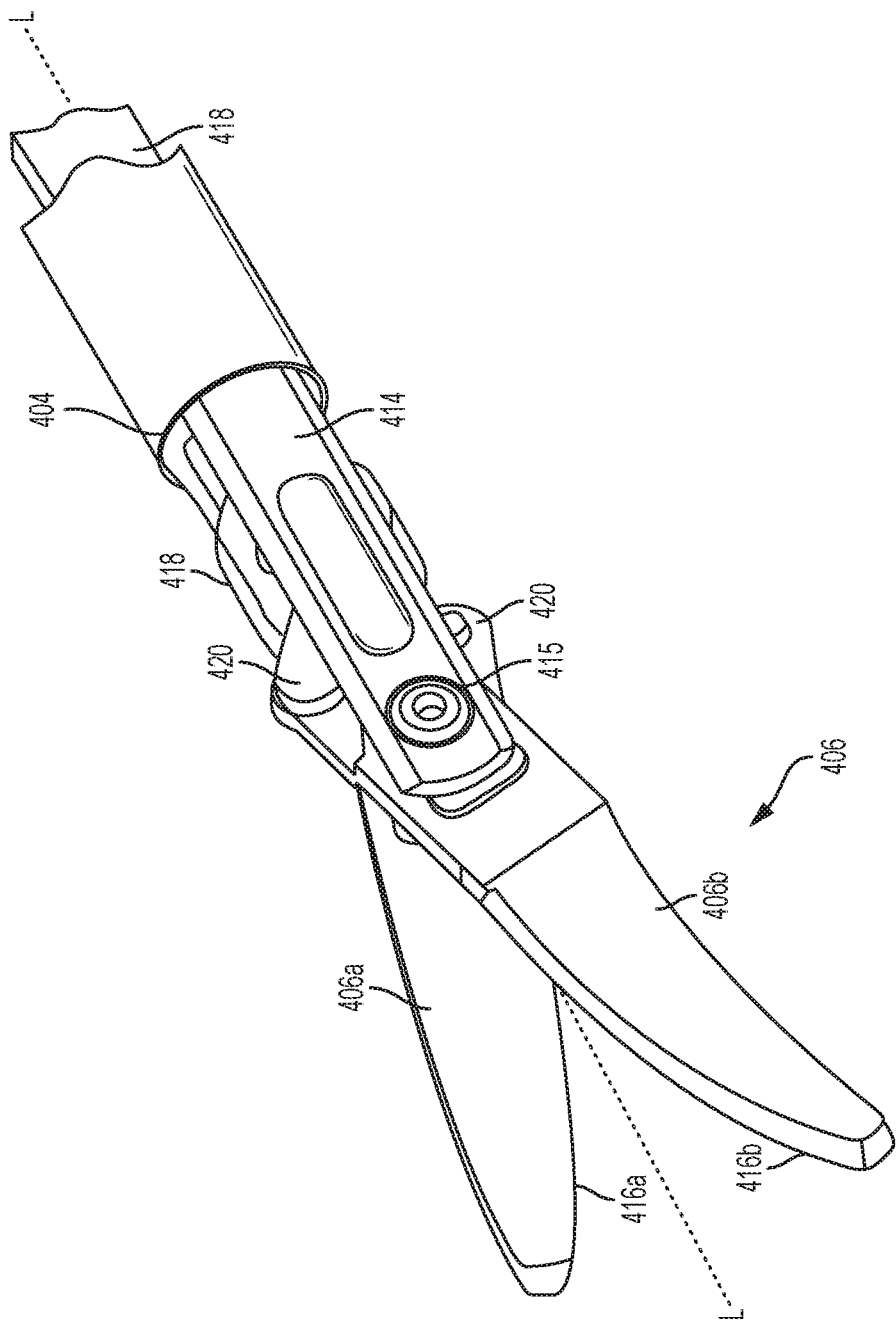

ELECTRICALLY-POWERED SURGICAL SYSTEMS

FIELD

Electrically-powered surgical systems and methods for using the same are provided for cutting or dissecting tissue.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices can be less precise in operation than manually-operated devices. For example, users of manually-operated devices are able to instantly stop the progress of a mechanism by simply releasing the actuation mechanism. With an electrically-powered device, however, releasing an actuation button or switch may not result in instantaneous halting of a mechanism, as the electric motor may continue to drive the mechanism until the kinetic energy of its moving components is dissipated. As a result, a mechanism may continue to advance for some amount of time even after a user releases an actuation button.

Accordingly, there remains a need for improved devices and methods that address current issues with electrically-powered surgical devices.

SUMMARY

Surgical systems and methods for using the same are provided herein.

In one exemplary embodiment, a surgical system is provided that can include an electromechanical tool having an instrument shaft and an end effector with an energy-delivering electrode disposed thereon, an electromechanical arm configured for movement with respect to multiple axes, where the electromechanical tool is configured to be mounted on the electromechanical arm, a motor operably coupled to the electromechanical tool and configured to drive insertion of the end effector into tissue at a treatment velocity, and a control system operably coupled to the motor and the electromechanical tool. The control system can be configured to measure a force acting upon the end effector when the end effector is moving at the treatment velocity, to determine a depth of insertion within tissue of the end effector, and to selectively control at least one of a power delivered to the electromechanical tool and the treatment velocity based on at least one of the determined force and the determined depth of insertion. In one aspect, the energy-delivery electrode can be a monopolar device.

In one aspect, the system can further include a machine vision system coupled to the control system and configured to determine the insertion depth of the end effector. In another aspect, the end effector can include indicia formed thereon.

In one aspect, the control system can be configured to lower the power delivered to electromechanical tool when the determined force exceeds a predetermined force threshold. In another aspect, the control system can be configured to lower the treatment velocity of the end effector when the determined force exceeds a predetermined force threshold. In yet another aspect, the control system can be configured to stop insertion of the end effector into the tissue when the determined force exceeds a predetermined force threshold.

In some aspects, the control system can be configured to selectively deliver power to the electromechanical tool at a first power setting and a second power setting that is greater than the first power setting, and the control system can be configured to drive insertion of the end effector at a first treatment velocity at the first power setting and at a second treatment velocity at the second power setting, the second power setting being greater than the first treatment velocity. In one aspect, the control system can be configured to lower the treatment velocity of the end effector when the control system is operated at the first power setting and the determined force exceeds a first predetermined force threshold or when the control system is operated at the second power setting and the determined force exceeds a second predetermined force threshold.

In another exemplary embodiment, a surgical system is provided that can include an electromechanical tool having an instrument shaft and an end effector with an energy-delivering electrode disposed thereon, an electromechanical arm configured for movement with respect to multiple axes, where the electromechanical tool is configured to be mounted on the electromechanical arm, a motor operably coupled to the electromechanical tool and configured to drive movement of the end effector through tissue at an insertion velocity, and a control system operably coupled to the motor and the electromechanical tool. The control system can be configured to determine a tissue type by measuring a force acting upon the end effector when the end effector is moving through the tissue and measuring a tissue impedance encountered by the end effector during movement through the tissue in which the control system can be further configured to require an affirmation by an operator that transition to a different type is desired. In one aspect, the energy-delivery electrode can be a monopolar device In one aspect, the control system can be configured to provide a signal to the operator when the control system determines the end effector has transitioned into the different tissue. In another aspect, the control system can be configured to modify or cease power delivery to the motor when the control system determines the end effector has transitioned into the different tissue.

In some aspects, the force acting upon the end effector for a first tissue type can be less than a first predetermined force threshold and the tissue impedance can be greater than a first predetermined impedance threshold. In one embodiment, the force acting upon the end effector for a second tissue type can be between the first and a second predetermined force threshold, and the tissue impedance can be between the first and a second predetermined impedance threshold. In such embodiments, the force acting upon the end effector for a third tissue type can be between the first and second predetermined force thresholds and the tissue impedance can be less than the second predetermined impedance threshold.

Methods for treating tissue are also provided. In one embodiment, the method can include actuating a motor to drive insertion of an end effector of an electromechanical tool into a tissue at an insertion velocity while the end effector is energized to deliver electrosurgical energy to the tissue, and measuring, through a control system operably coupled to the motor and the electromechanical tool, a force acting upon the end effector and a tissue impedance encountered by the end effector when the end effector is moving through the tissue, where the control system modifies the power delivery to the motor when the end effector encounters a different type of tissue. In one aspect, the method can also include providing an affirmation to the control system that transition into the different type of tissue is desired.

In one aspect, modification of the power delivery can include ceasing power to the motor. In another aspect, modification of the power delivery can include increasing power to the motor when the tissue impedance of the tissue is less than a tissue impedance of the different type of tissue. In yet another aspect, modification of the power delivery can include decreasing power to the motor when the tissue impedance of the tissue is greater than a tissue impedance of the different type of tissue.

In an exemplary embodiment, a surgical system is provided and can include an electromechanical tool, an electromechanical arm that is configured for movement with respect to multiple axes and to be mounted on the electromechanical arm, and a control system operably coupled to the electromechanical arm and the electromechanical tool for controlling movement thereof. The electromechanical tool can include an instrument shaft and an end effector with an energy-delivering electrode disposed thereon, where the electrode is configured to deliver energy to tissue. The control system can also be configured to determine a zone of avoidance surrounding the electromechanical tool when energy is delivered to tissue through the electrode and, when entry into the zone of avoidance by a secondary electromechanical tool is determined by the control system to be imminent, the control system can be configured to do at least one of reduce a power level at which energy is delivered to the tissue by the electrode and prevent the secondary electromechanical tool from entering the zone of avoidance. In one aspect, the zone of avoidance can be dependent at least on a power level at which the electrode is energized.

In one embodiment, at least a portion of the secondary electromechanical tool can be formed of a conductive material.

In another embodiment, the secondary electromechanical tool can be configured to be mounted to the electromechanical arm or a secondary electromechanical arm and the control system can be configured to be operably coupled to the secondary electromechanical tool. In such instances, when entry into the zone of avoidance by the secondary electromechanical tool is imminent, the control system can be configured to maintain the power level and redirect the secondary electromechanical tool relative away from the zone of avoidance to prevent the secondary electromechanical tool from entering the zone of avoidance.

In one embodiment, when the power level is reduced, a size of the zone of avoidance can be reduced to prevent entry of the secondary electromechanical tool into the zone of avoidance and the reduced size of the zone can be maintained.

In another embodiment, the control system can be configured to detect a first energy level of the secondary electromechanical tool relative to a second energy level to determine when entry into the zone of avoidance is imminent. In one aspect, the second energy is ground. In yet another embodiment, the control system can be configured to detect a distance of the secondary electromechanical tool relative to the zone of avoidance to determine when entry into the zone of avoidance is imminent.

Methods for operating a surgical system are also provided. In one embodiment, the method can include actuating an electromechanical arm to position an electromechanical tool mounted thereon for insertion into tissue in which the electromechanical tool includes an instrument shaft and an end effector that includes an energy-delivering electrode disposed thereon and configured to deliver energy to the tissue, and inserting at least the end effector into the tissue. The method can also include determining, through a control system operably coupled to the electromechanical arm and the electromechanical tool, a zone of avoidance surrounding the electromechanical tool when energy is delivered to tissue through the electrode, and when the control system determines that entry into the zone of avoidance by a secondary electromechanical tool is imminent, the control system can reduce a power level at which energy is delivered to the tissue by the electrode or can prevent the secondary electromechanical tool from entering the zone of avoidance. In one aspect, the zone of avoidance can be dependent at least on a power level at which the electrode is energized. In another aspect, at least a portion of the secondary electromechanical tool can be formed of a conductive material.

In one aspect, when entry of the secondary electromechanical tool into the zone of avoidance is imminent, the method can also include reducing, through the control system, the power level to reduce a size of the zone of avoidance to prevent entry of the secondary electromechanical tool into the zone of avoidance. In another aspect, when entry of the secondary electromechanical tool into the zone of avoidance is imminent, the method can also include redirecting, through the control system being operably coupled to the secondary electromechanical tool, the secondary electromechanical tool away from the zone of avoidance.

In some aspects, the method can also include detecting, through the control system, a first energy of the secondary electromechanical tool relative to a second energy to determine when entry into the zone of avoidance is imminent. In one aspect, the second energy is ground. In other aspects, the method can also include detecting, through the control system, a distance of the secondary electromechanical tool relative to the zone of avoidance to determine when entry into the zone of avoidance is imminent.

In an exemplary embodiment, a surgical system is provided and can include an electromechanically tool having a housing and an instrument shaft extending therefrom with an end effector at a distal end of the shaft and includes a pair of cutting blades with sharpened surfaces facing each other, an actuator rod operably coupled to the end effector and extending through the shaft, a motor operably coupled to the actuator rod and configured to actuate the actuator rod, and a control system that is configured to monitor motor torque and to cease blade closure when the motor torque exhibits a predetermined magnitude after a predetermined range of blade closure. The actuator rod can be configured to selectively move the cutting blades between an open configuration and a closed configuration such that when the actuator rod is actuated, by the motor, the cutting blades are moved from the open position to the closed configuration.

In one aspect, the end effector can be monopolar. In another aspect, the pair of cutting blades can be determined to be of sufficient sharpness when the motor torque exhibits the predetermined magnitude.

The housing can have a variety of configurations. For example, in one aspect, the housing can include a tool mounting portion that is configured to mount on a motor housing a surgical robot.

In another exemplary embodiment, a surgical system is provided and can include an electromechanical tool having a housing an instrument shaft assembly extending therefrom, a motor, and a control system having a predetermined threshold for a motor force corresponding to each of a plurality of insertion depths. The instrument shaft assembly can have at a distal end thereof an end effector that includes a pair of jaws and can have an actuator extending through the shaft assembly and operably coupled to the end effector in which the actuator can be configured to selectively move the jaws between an open configuration and a closed configuration. In one aspect, the end effector is monopolar. The motor can be operably coupled to the actuator and can be configured to actuate the actuator to effect movement of the jaws between the open and closed configurations. The control system can be configured to determine a depth of insertion of the jaws into tissue and to determine the motor force during jaw opening and further configured to permit jaw opening at a predetermined velocity until the motor force exceeds the predetermined threshold corresponding to the determined depth of insertion and thereafter limit the motor force during jaw opening so that the motor force does not exceed the predetermined threshold for the determined insertion depth. In one aspect, the jaw opening can occur at a reduced velocity relative to the predetermined velocity when the motor force exceeds the predetermined threshold.

In some aspects, the end effector can include at least one pair of sensors in communication with the control system and the at least one pair of sensors can be configured to provide the depth of insertion of the jaws into tissue to the control system. In such aspects, for example, the at least one pair of sensors can include a first pair of sensors having opposing first and second sensors. A first jaw of the pair of jaws can include the first sensor and a second jaw of the pair of jaws can include the second sensor.

The housing can have a variety of configurations. For example, in one aspect, the housing can include a tool mounting portion that is configured to mount a motor housing on a surgical robot.

Surgical methods are also provided. In one embodiment, the method can include inserting into tissue an end effector having opposed pivotable jaws that are configured to be moved between open and closed configurations and determining through a control system a depth of insertion of the jaws. The method can also include controlling opening of the jaws through the control system such that the jaws open at a predetermined velocity until a force on a motor driving jaw opening exceeds a predetermined threshold for the determined depth of insertion and thereafter limiting the motor force during jaw opening so that the motor force does not exceed the predetermined threshold for the determined insertion depth.

In one aspect, when the motor force exceeds the predetermined threshold, the method can also include reducing velocity during jaw opening. In another aspect, the method can also include actuating a motor operably coupled to the end effector to move the jaws between the open and closed configurations.

In other aspects, the end effector can include at least one pair of sensors in communication with the control system, and the determining the depth of insertion includes sensing the depth of insertion of the jaws using the at least one pair of sensors, and providing the depth of insertion to the control system.

BRIEF DESCRIPTION OF THE DRAWINGS

This invention will be more fully understood from the following detailed description taken in conjunction with the accompanying drawings, in which:

FIG. 7B is a perspective view of a distal portion the surgical cutting device of FIG. 7A;

DETAILED DESCRIPTION

Figure 1:
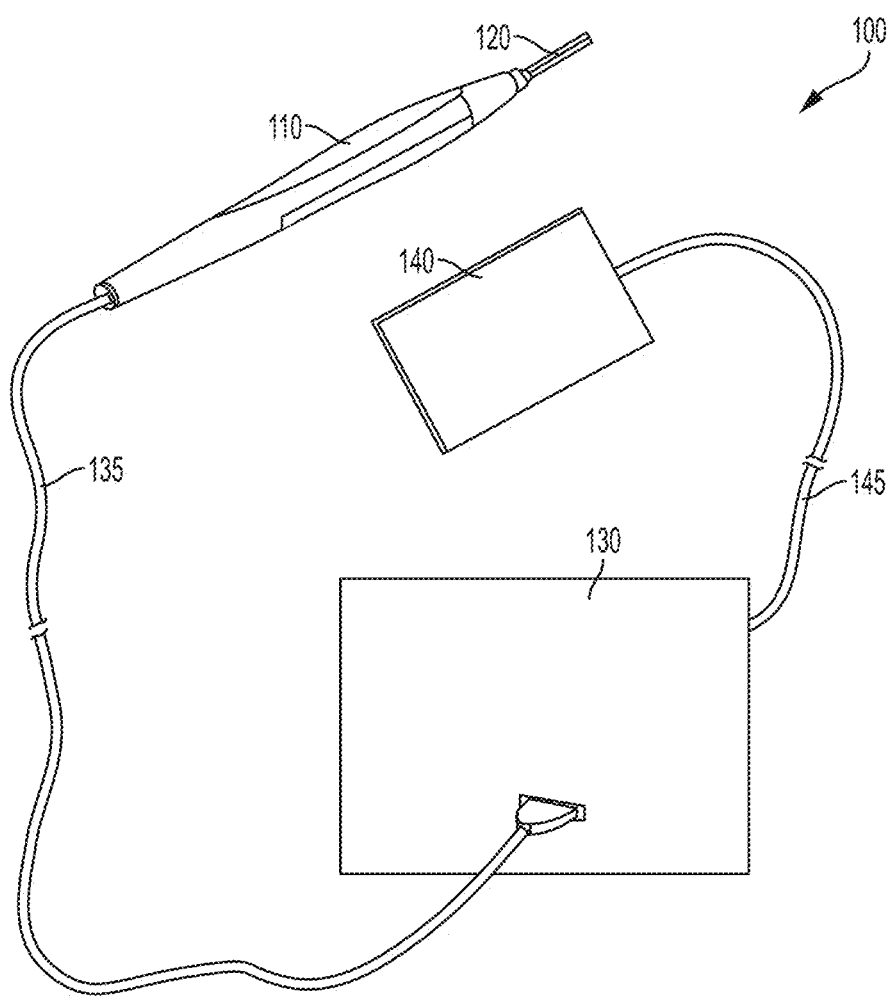
FIG. 1 is a perspective view of one exemplary embodiment of a monopolar electromechanical device system.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Surgical systems and methods for using the same during a surgical procedure are provided. During surgery, situational awareness enables effective use of a surgical device. While more and more surgical procedures are being performed using electrically-powered surgical devices that are either hand-held or that are coupled to a surgical robotic system, these surgical devices lack real-time feedback, tactile or otherwise, and therefore inhibits a user's ability to effectively, accurately, and safely use these devices. The surgical systems described herein are configured to provide real-time feedback during surgery so that a user or robot can modify the surgical plan in real-time, if necessary, to avoid injury in an unintended area of tissue and/or damage to the surgical device itself.

In general, the surgical systems described herein at least include an electromechanical tool having an end effector and a control system. The end effector can be designed for cutting tissue, e.g., a single cutting blade or a pair of cutting blades, or for dissecting tissue. Depending on the design of the end effector, the surgical system can include one or more motors that actuate the electromechanical tool and/or one or more generators that energize the electromechanical tool.

Motors

In general, one or more motors can be used to drive various surgical device functions. The device functions can vary based on the particular type of surgical device, but in general a surgical device can include one or more motors that can be configured to cause a particular action or motion to occur, such as opening and/or closing of cutting blades or jaws, shaft and/or end effector rotation, end effector articulation, firing to deliver an implantable component such as a clip, staple, adjunct, etc., energy delivery, etc. The motor(s) can be located within the surgical device itself or, in the alternative, coupled to the surgical device such as via a robotic surgical system. Each motor can include a rotary motor shaft that is configured to couple to or interact with one or more elements of the surgical device, e.g., an actuator or actuator rod, so that the motor can actuate the one or more elements to cause a variety of movements and actions of the device, e.g., to selectively move cutting blades or jaws of an end effector between an open configuration and a closed configuration. The motor(s) can be powered using various techniques, such as by a battery on the device or by a power source connected directly to the device or connected through a robotic surgical system.

Additional components, such as sensors or meter devices, can be directly or indirectly coupled to the motor(s) in order to monitor a force on the motor during actuation of the device. For example, a torque sensor can be coupled to the motor to determine or monitor an amount of force being applied to the motor during device operation. It is also contemplated that another way to determine or monitor force on the motor can include measuring current though the motor by using a sensor or a meter device.

In certain embodiments, as discussed in more detail below, when the at least one motor is activated, its corresponding rotary motor shaft drives the rotation of at least one corresponding gear assembly located within the drive system of the surgical device, such as surgical devices 500 and 700 in FIGS. 9B and 13B, respectively. The corresponding gear assembly can be coupled to at least one correspondimg drive shaft, thereby causing linear and/or rotational movement of the at least corresponding drive shaft. While movement of two or more drive shafts can overlap during different stages of operation of the drive system, each motor can be activated independently from each other such that movement of each corresponding drive shaft does not necessarily occur at the same time or during the same stage of operation.

When the at least one drive shaft is being driven by its corresponding motor, a rotary encoder, if used, can determine the rotational position of the motor, thereby indicating linear or rotational displacement of the at least one drive shaft. Additionally or in the alternative, when the corresponding motor is activated, the torque sensor, if used, can determine the force on the motor during linear or rotary movement of the at least one drive shaft.

Operation of Control System

Generally, as discussed in more detail below, the control system can control movement and actuation of a surgical device. For example, in one embodiment, the control system can include at least one computer system and can be operably coupled to at least one motor that drives the end effector the surgical device through tissue or that drives a drive system on the surgical device. Alternatively, or in addition, the at least one computer system can control power delivery to a surgical device and/or motors of an electromechanical arm. The computer system can include components, such as a processor, that are configured for running one or more logic functions, such as with respect to a program stored in a memory coupled to the processor. For example, the processor can be coupled to one or more wireless or wired user input devices ("UIDs"), and it can be configured for receiving sensed information, aggregating it, and computing outputs based at least in part on the sensed information. These outputs can be transmitted to a drive system and/or to a power source, such as a generator, of the surgical device to control the surgical device during use.

Monopolar Electrosurgery

Any of the surgical devices described herein can function as a monopolar device. An exemplary embodiment of a monopolar electromechanical device system 100 is illustrated in FIG. 1. As shown, the electromechanical tool 110 includes an active electrode 120 that serves as the end effector and that is connected to the generator 130 via connector 135. In some embodiments, the active electrode 120 can be disposed on or in the end effector. In other embodiments, the generator 130 can be operably connected to a wire or other electrical conductor that extends through the electromechanical tool 110 and is coupled to the end effector.

As shown in FIG. 1, a patient return electrode 140 is also coupled to the generator 130, and, before energizing the active electrode 120, the patient return electrode 140 is placed on the patient's body. When activated, the generator 130 creates electrosurgical energy, such as radio frequency (RF) electrical energy, that flows to the active electrode 120 thereby energizing the electrode 120 and then from the active electrode 120 into the tissue. The energy then passes through the patient as it completes the circuit from the active electrode 120 to the patient return electrode 140 and then returns to the generator 130 via a connector 145. As such, the generator 130 can regulate the electrical energy delivered to the active electrode 120, and effectively to the patient, during surgery. Further, as described in more detail below, a control system can be operably coupled (wired or wirelessly) to the generator 130 to activate the generator 130 and control the energy delivered to the active electrode 120 during surgery.

An exemplary surgical system can include a variety of features to facilitate application thereof as described herein and illustrated in the drawings. However, a person skilled in the art will appreciate that the surgical systems can include only some of these features and/or it can include a variety of other features known in the art. The surgical systems described herein are merely intended to represent certain exemplary embodiments. Moreover, while the control systems are described in connection with surgical devices for cutting and/or dissecting tissue, a person skilled in the art will appreciate that these systems can be used in connection with other surgical devices, such as needle drivers, staplers, clip appliers/removers, suction tools, irrigation tools, etc. Further, a person skilled in the art will appreciate that the surgical systems described herein have application in conventional minimally-invasive and open surgical instrumentation as well as application in robotic-assisted surgery.

Surgical Devices

A. Cutting Devices

In general, the surgical systems described herein below that are configured for cutting tissue include an electromechanical tool having an end effector designed for cutting tissue, e.g., a single cutting blade or a pair of cutting blades, and a control system. Depending on the design of the end effector, the surgical system can include one or more motors and/or one or more generators that actuate and energize, respectively, the electromechanical tool. Moreover, while the control system can have a variety of configurations for each surgical system, the control system advantageously provides real-time feedback to a user or robotic system during surgery, providing situational awareness to the user/robot, thereby allowing the user/robot to move and/or cease movement of the electromechanical tool during surgery. For example, in one embodiment, the control systems described herein can provide feedback to the user or robotic system that the tool has reached a particular insertion depth and selectively control the power being delivered to the device and/or the treatment velocity to keep the end effector is a substantially longitudinal straight configuration during tissue cutting and/or to avoid unintentional damage to tissue. In another embodiment, the control system can be configured to determine when the tool has encountered a different type of tissue. In another embodiment, during surgery, the control system can be configured to determine when a cut is completed and, when the cut is complete, cease blade closure, thereby preventing damage to tissue and/or the device itself.

i. Single Blade

In certain aspects, the surgical systems for cutting tissue can include an electromechanical tool having an instrument shaft and an end effector with an energy-delivering electrode disposed thereon, an electromechanical arm configured for movement with respect to multiple axes, a motor operably coupled to the electromechanical tool and configured to drive insertion of the end effector into tissue at a treatment velocity, and a control system operably coupled to the motor and the electromechanical tool. In some aspects, the motor as well as the control system can be disposed within a tool housing of the electromechanical tool, or it can be located outside of the electromechanical tool, such as within a surgical robotic system.

While the end effector can include a variety of configurations for cutting tissue, in some implementations, the end effector can include a single cutting blade. In one embodiment, the single cutting blade is monopolar in which case an electrode can be disposed on or into the single cutting blade. Alternatively, the electrode can be the single cutting blade. In either case, the cutting blade is initially dull, and when it is energized, e.g., by a generator, it effectively becomes sufficiently sharp to cut tissue.

Figure 2A:
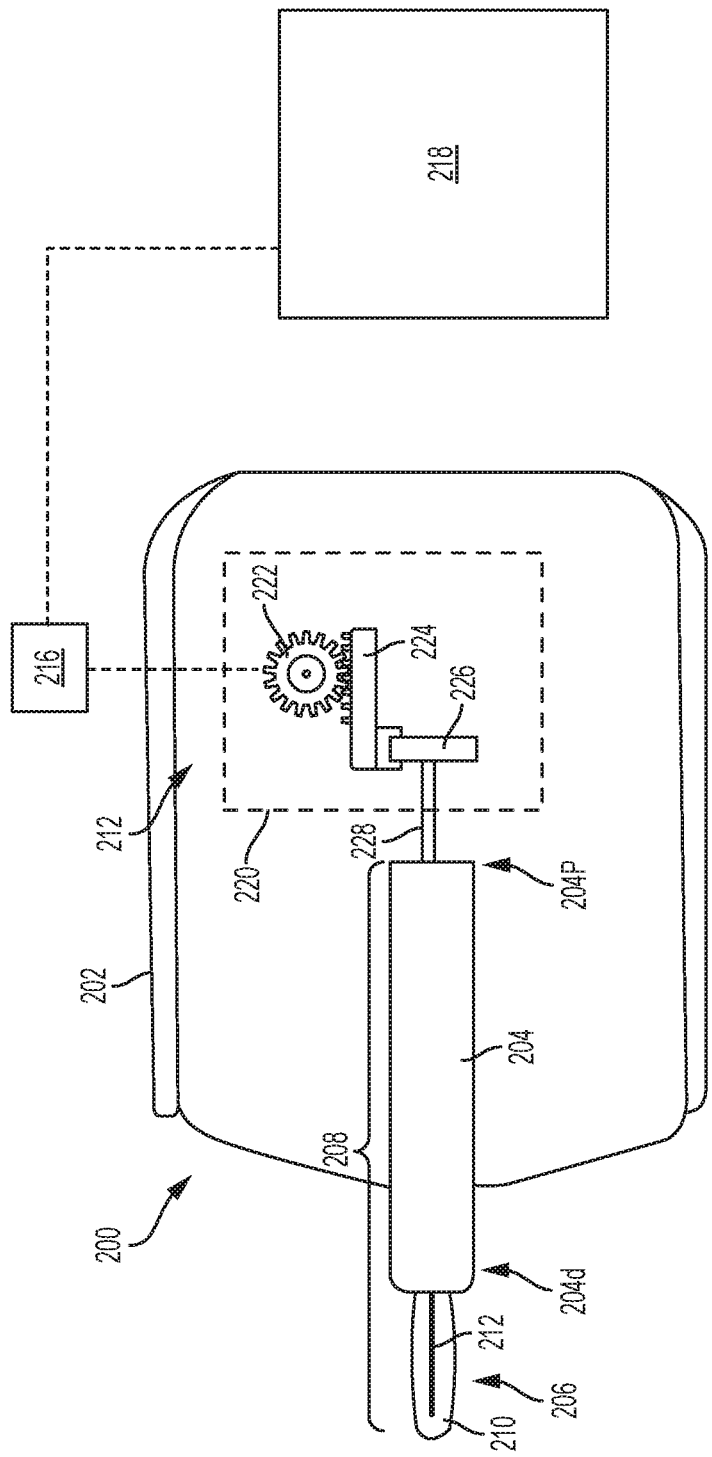
FIG. 2A is a side, partially transparent schematic view of an exemplary cutting device having a single cutting blade and coupled to a drive system, the drive system being coupled to motors that are operably coupled to a control system.

As indicated above, in an exemplary embodiment control systems are provided for controlling actuation and movement of a surgical device. FIG. 2A illustrates a monopolar cutting device 200 for use with a control system. As shown, the device 200 has a tool housing 202, an instrument shaft 204 that extends therefrom, and an end effector 206 attached to the distal end 204d of the instrument shaft 204. The instrument shaft 204 and end effector 206 are collectively referred to herein as an instrument shaft assembly 208. While the end effector 206 can have a variety of configurations, in this exemplary embodiment, the end effector 206 is a single cutting blade 210 with an electrode 212 disposed thereon. In one embodiment, the single cutting blade 210 includes indicia formed thereon, which can be used to determine the insertion depth of the blade 210 into tissue.

Figure 2B:
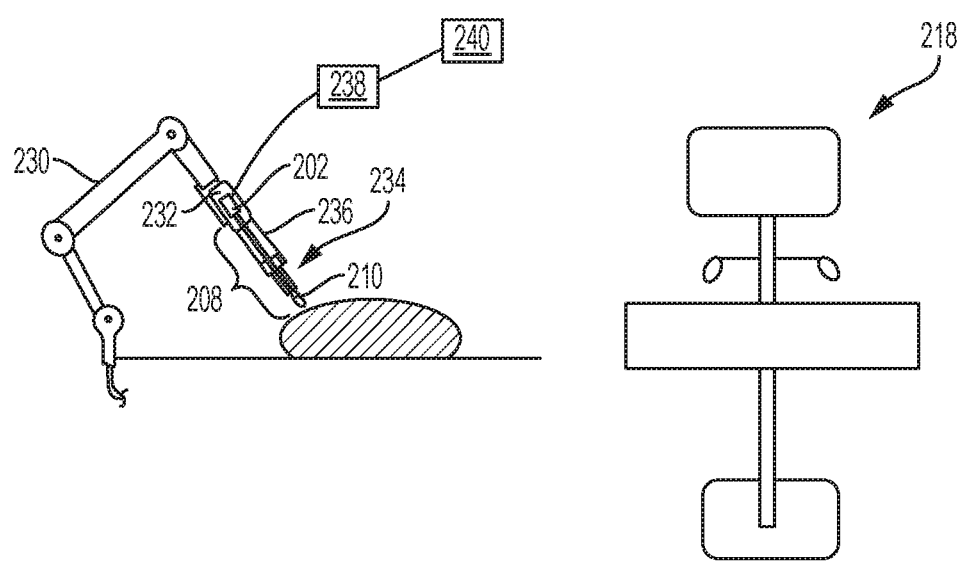
FIG. 2B is a perspective view of an exemplary embodiment of a surgical system that includes the cutting device of FIG. 2A coupled to a generator and to a robotic arm each being wirelessly coupled to a control system, and the robotic arm having the drive system mounted in a motor housing on an end of the robotic arm.

As shown in FIG. 2A, the electrode 212 is operatively coupled to a generator, like generator 238 in FIG. 2B. A bore (not shown) of the instrument shaft 202 can carry electrical leads to wires that can deliver electrical energy from the generator 238 to the single cutting blade 210. As discussed above and illustrated in FIG. 2B, a patient return electrode 240 is coupled to the generator 238 and placed on a patient before energizing the electrode 212. Exemplary embodiments and further details on monopolar cutting blades are described in U.S. Patent Application Nos. 2016/019918 and 2016/019919, each of which is incorporated by reference herein in its entirety.

Figure 3:
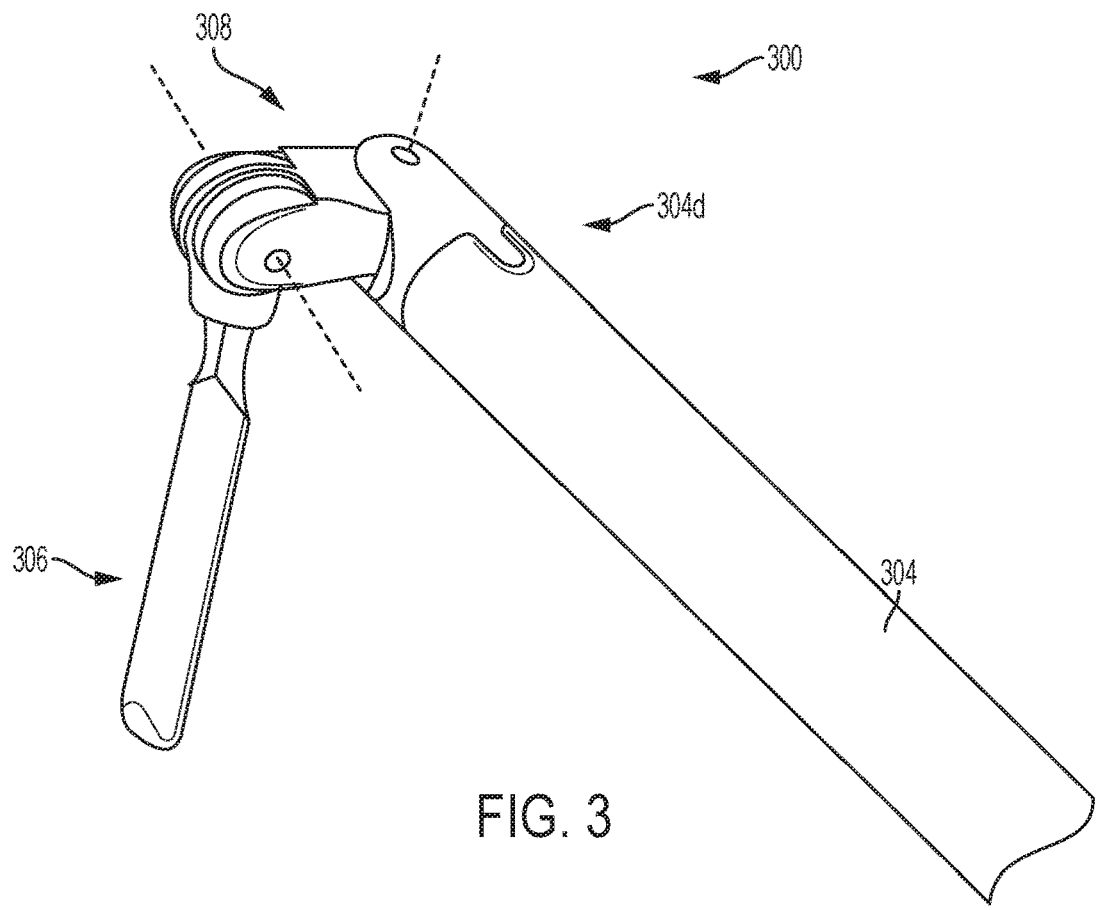
FIG. 3 is a perspective side view of a distal portion of another exemplary surgical cutting device having a single cutting blade.

In another embodiment, as shown in FIG. 3, the end effector 306 can be coupled to the distal end 304d of the instrument shaft 304 via a wrist 308. The wrist 308 can have any of a variety of configurations. Exemplary embodiments of a wrist of a surgical tool are described in International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, which are hereby incorporated by reference in their entireties. In general, the wrist 308 can include a joint configured to allow movement of the end effector 306 relative to the shaft 304, such as a pivot joint at which he the end effector 306 is pivotally attached. In some embodiments, the pivoting motion can include pitch movement about a first axis of the wrist 308 (e.g., a X axis), yaw movement about a second axis of the wrist 125 (e.g., a Y axis), and combinations thereof to allow for 360° rotational movement of the end effector 306 about the wrist 308. In other embodiments, the pivoting motion can be limited to movement in a single plane, e.g., only pitch movement about the first axis of the wrist 308 or only yaw movement about the second axis of the wrist 308, such that end effector 306 rotates in a single plane.

The surgical device 300 can include one or more linkage members (not shown) configured to effect the movement of the end effector 306 relative to the shaft 304. The linkage members are operably coupled to a tool housing (not shown), extend within the shaft 304, extend at least partially through the wrist 308, and are operably coupled to the end effector 306. In an exemplary embodiment, the linkage members extend distally from the tool housing along the shaft 304 within an inner lumen of the shaft 304. The linkage members can have any of a variety of configurations, for example cables, rods, wires, or twisted cables. The linkage members can be selectively actuated to cause the end effector 306 to pivot at the wrist 308 relative to the shaft 304. The selective actuation of the linkage members can cause any one or more of the linkage members to move, e.g., translate longitudinally, to cause the articulation. The one or more of the linkage members that translate depending on the requested articulation, e.g., to cause the end effector 306 to yaw and/or pitch as requested. The actuation can be accomplished in any of a variety of ways, such as by actuating an actuation mechanism operably coupled to the tool housing. Exemplary embodiments of such actuation mechanisms and additional details are disclosed in U.S. patent application Ser. No. 15/422,767 to Mark D. Overmyer et al. filed on Feb. 2, 2017, the disclosure of which is herein incorporated by reference in its entirety.

Referring back to FIG. 2A, the tool housing 202 contains a drive system 214 that is shown coupled to a motor 216 that is operably coupled to a control system 218. A person skilled in the art will appreciate that the motor 216 and control system 218 can be located within the tool housing 202 to form a powered hand-held device, or they can be located external of the housing 202, such as in a robotic system as described with respect to FIG. 2B.

While the drive system 214 can have a variety of configurations. For example, as shown in FIG. 2A, the drive system 212 includes a drive assembly 220 configured to advance the instrument shaft assembly 208 in distal and proximal directions relative to the housing 202 to cause the end effector 206 to be inserted into and to be removed from tissue. The drive assembly 220, which is discussed in more detail below, can be coupled to a rotary motor shaft of a corresponding motor, which in the illustrated embodiment (FIG. 2B) is disposed in a tool housing 202 on the end of the robotic arm 230. During actuation, the corresponding motor 216 can actuate the drive system 214 and thus the drive assembly 220. Further, the motor 216 can be coupled to a rotary sensor that provides the control system 218 with information about the depth insertion of the cutting blade 210 within tissue. Exemplary motors for use with the systems disclosed herein are described, for example, in U.S. Pat. Nos. 9,445,816 and 9,585,658 and in U.S. Patent Publication Nos. 2012/0292367 and 2015/0209059, each of which is incorporated herein its entirety.

The drive assembly 220 can have a variety of configurations. For example, as shown in FIG. 2A, the drive assembly 220 can include a rotary drive gear 222 that is in meshing engagement with a rack 224 that is coupled to a drive bracket 226 having a drive shaft 228 extending therefrom and in contact with the proximal end 204*p* the instrument shaft 204. The rotary drive gear 222 can be operably coupled to the motor 216. In use, when the motor 216 is activated by the control system 218 and its corresponding rotary motor shaft drives the rotation of the rotary drive gear 222, thereby causing linear movement of the instrument shaft assembly 208. It will be appreciated that the application of a rotary output motion from the motor 216 in one direction will result in the linear movement of the instrument shaft assembly 208 in a distal direction to insert the cutting blade 210 into tissue. Further, application of the rotary output motion in an opposite direction will result in the linear movement of the instrument shaft assembly 208 in a proximal direction to retract the instrument shaft assembly 208 so as to, e.g., remove the cutting blade 210 from tissue.

Over the years a variety of minimally invasive robotic (or "telesurgical") systems have been developed to increase surgical dexterity as well as to permit a surgeon to operate on a patient in an intuitive manner. Many of such systems are disclosed in the following U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,132,368, entitled "Multi-Component Telepresence System and Method", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled "Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors". Many of such systems, however, have in the past been unable to generate the magnitude of forces required to effectively cut and fasten tissue.

FIG. 2B illustrates a robotic arm 230 wirelessly coupled to a control system 218 having a console with a display and two user input devices. One or more motors (not shown) are disposed within a motor housing 232 that is coupled to an end of the robotic arm 230. The tool housing 202 of the surgical cutting device 200 is mounted to the motor housing 232 to thereby operably couple the motor to the drive system 212. As a result, when the motors are activated by the control system 218, the motor can actuate the drive system 214. As shown in FIG. 2B, the instrument shaft assembly 208 extends from the tool housing 202. During surgery, the instrument shaft assembly 208 can be placed within and extend through a trocar 234 that is mounted on the bottom of a carrier 236 extending between the motor housing 232 and a trocar support. The carrier 236 allows the instrument shaft assembly to be translated into and out of the trocar 234. Further, given that the surgical cutting device is monopolar, a generator 238 is operably coupled to the electrode 212 disposed on the cutting blade 210 and is operably coupled to a patient electrode 240 that is placed on a patient prior to energizing the electrode. In use, when the generator 238 is activated, by the control system 218, the generator 238 delivers electrical energy to the electrode 212 thereby energizing the electrode 212, and consequently the cutting blade 210 so that the cutting blade 210 becomes sufficiently sharp to cut tissue. The robotic arm 230 is configured to support and move the surgical device 200 along one or more degrees of freedom (e.g., all six Cartesian degrees of freedom, five or fewer Cartesian degrees of freedom, etc.). For example, once the cutting blade is inserted into tissue at the desired depth, the robotic arm is configured (e.g., with a motor) to laterally advance the cutting blade through the tissue.

Exemplary embodiments of motor operation and components of a tool or drive system housing (also referred to as a "puck") configured to be controlled by motors are further described in International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, each of which is hereby incorporated by reference in its entirety.

Figure 4A:
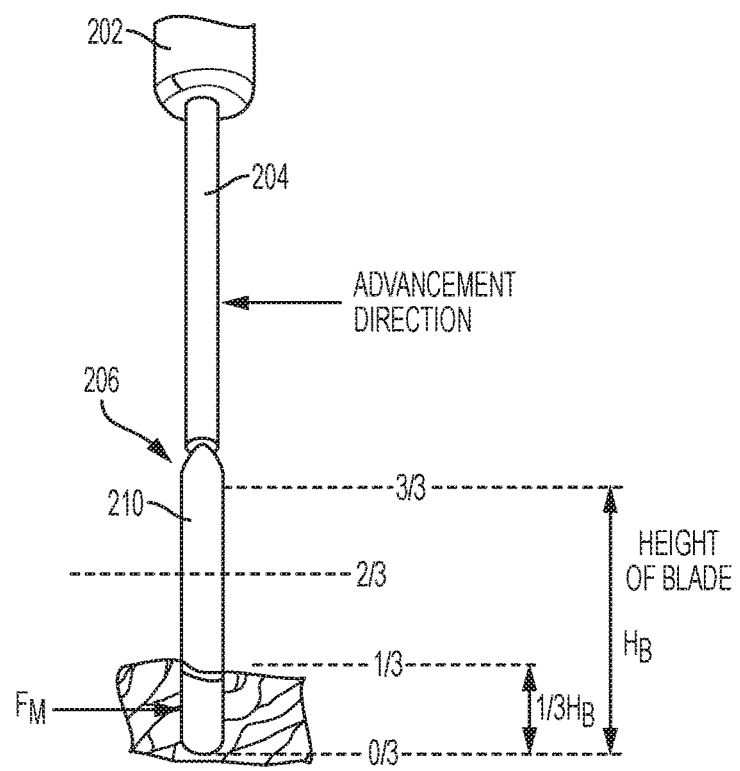
FIG. 4A is side perspective view of a distal portion of the cutting device of FIG. 2A showing a portion of the cutting blade (about one-third of the height) inserted into tissue.

As discussed above, the control system can control movement and actuation of a surgical device. When the control system is actuated, it drives one or more motors on or coupled to the surgical device, consequently actuating the drive system to insert the cutting blade into tissue. Once the cutting blade is inserted into tissue, the control system actuates the robotic arm to laterally move the cutting blade through the tissue at a treatment velocity thereby cutting the tissue. It is desirable for the cutting blade to remain substantially straight as it moves through tissue, as shown in FIG. 4A. However, during lateral movement through tissue, the cutting blade encounters a lateral drag, $F_M$ shown in FIG. 4A, that can cause the cutting blade to tilt, which is undesirable. Furthermore, in general, it can be also desirable to cauterize the tissue as it is being cut. As such, as the cutting blade advances through tissue, a particular energy density is needed for cauterizing. However, when the cutting blade is tilted, the blade can be advancing at a treatment velocity that does not provide a power ratio that is high enough to provide the particular energy density needed to cauterize the cut tissue.

Accordingly, various embodiments of control systems are provided for producing real-time feedback during the operation of electrically-powered surgical devices so as to enable a user or robot to effectively and accurately use such devices. In general, once the end effector is inserted into tissue, the control system can be configured to measure a force acting upon the end effector when the end effector is moving at a treatment velocity and to determine a depth of insertion within tissue of the end effector. In addition, the control system can be configured to selectively control at least one of a power delivered to tissue by the end effector and the treatment velocity based on at least one of the determined force and the determined depth of insertion. In this way, the control system can modify the operation of the device such that the cutting blade remains substantially straight during cutting and/or the cut tissue can be cauterized.

In certain embodiments, the control system can be a closed-loop feedback system. The stored data within the computer system can include predetermined force thresholds for specific insertion depths of the cutting blade. The insertion depths of the cutting blade are related to the height of the cutting blade, $H_B$ shown in FIG. 4A. The greater the insertion depth, the greater the predetermined force threshold for laterally moving the cutting blade through tissue. During operation, the control system can receive feedback input from one or more sensors that are coupled to the motor(s) of the robotic arm that advance the cutting blade and that sense the torque of the motor(s), and consequently, the force acting upon the end effector during movement through tissue. In addition, the control system can receive input from a machine vision system that is coupled to the control system and that is configured to determine the insertion depth of the cutting blade. The computer system can aggregate the received feedback input(s), perform any necessary calculations, compare it to a predetermined force threshold for the determined insertion depth, and provide output data to the motor(s).

Figure 4B:
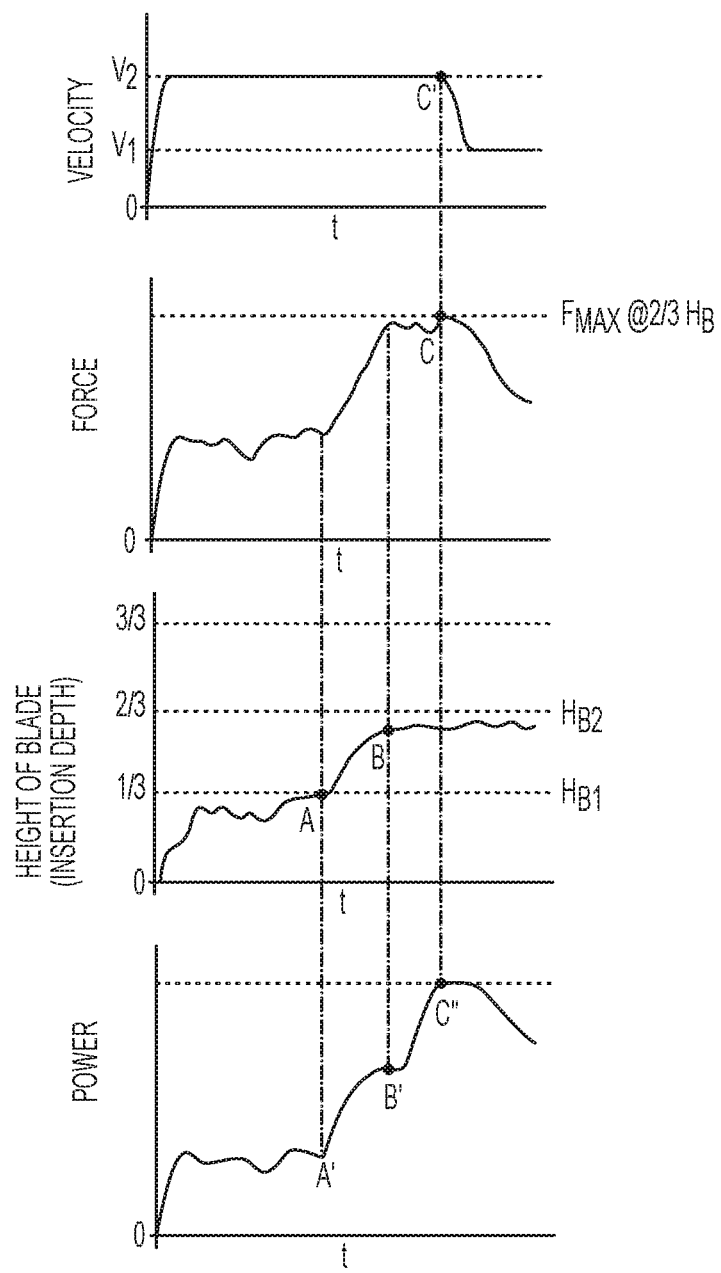
FIG. 4B is a graph illustrating a process for controlling the motor force of the robotic arm being applied to the cutting blade of FIG. 2A during its advancement through tissue.

In one embodiment, if at any time during operation the control system determines that the received input meets or exceeds the predetermined force threshold for the determined insertion depth, e.g., $F_{MAX}$ for $H_{B2}$ as shown in FIG. 4B, the control system can modify the output data sent to the motor(s) based on the programmed logic functions. For example, as shown in FIG. 4B, the control system can modify the output data sent to the motor(s) to decrease the treatment velocity, i.e., from $V_2$ to $V_1$.

Figure 5:
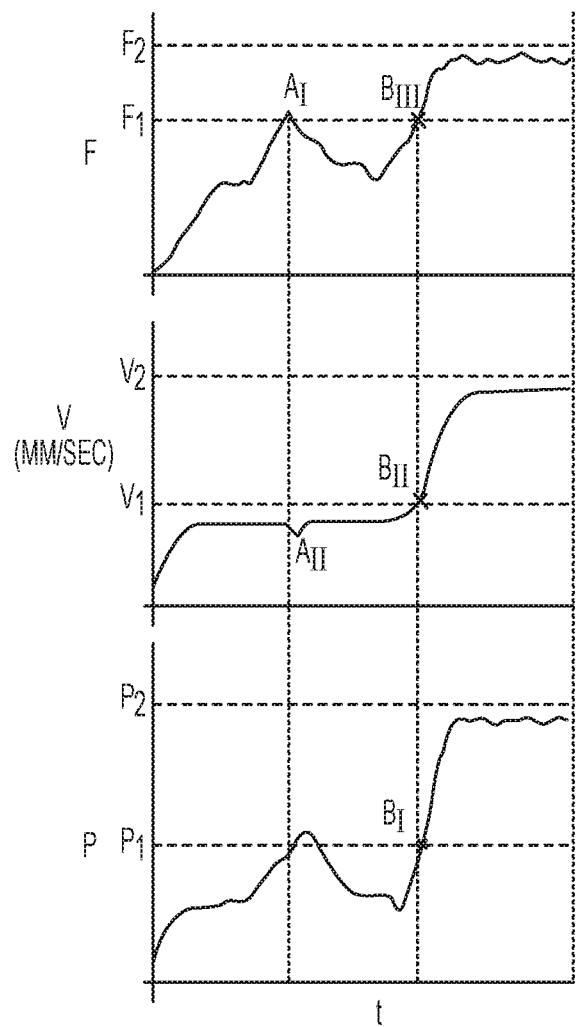
FIG. 5 is a graph illustrating a process for controlling the motor force being applied to the cutting blade of FIG. 2A during actuation of the drive system at two different power settings.

In another embodiment, the control system can be configured to monitor the force (F) as well as the advancement velocity (V) at various power settings, as shown in FIG. 5. In this exemplary embodiment, if the device is operating at a first power setting, such as 40 W, and the control system determines that the force exceeds a predetermined force threshold, $F_1$, at time $A_I$, as shown in FIG. 5, the control system can be configured to modify the advancement velocity in order to compensate and to reduce the overall power requirements of the device below the predetermined power threshold $P_1$ for the first power setting. In certain instances, the control system can also be configured to modify the power setting of the device directly, such as increase the power setting from a first power setting to a second power setting. For example, as shown in FIG. 5, when the device is operating at a first power setting, as the force increases above the predetermined force threshold $F_1$, shown at $B_{III}$, and the advancement velocity is increased by a user to exceed the predetermined velocity threshold, $V_1$, shown at $B_{II}$, the control system can be configured to increase the first power setting to a second power setting, such as from 40 W to 60 W, at $B_I$, as shown in FIG. 5. In this way, the predetermined velocity threshold is then increased from $V_1$ to $V_2$ and the predetermined force threshold is then increased from $F_1$ to $F_2$ to allow the electromechanical tool to be operated at the increased advancement velocity rate.

Figure 6B:
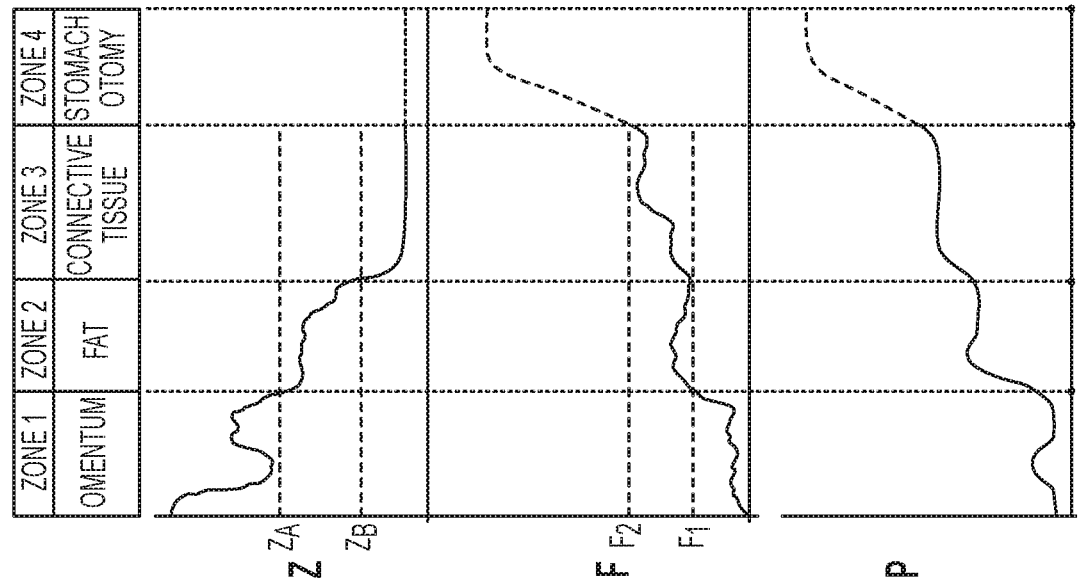
FIG. 6B is a graph illustrating a process for controlling the motor force being applied to the cutting blade during actuation of the motor of the robotic arm in FIG. 2B when the cutting blade encounters different types of tissue and, if desired, advances therethrough.
Figure 6A:
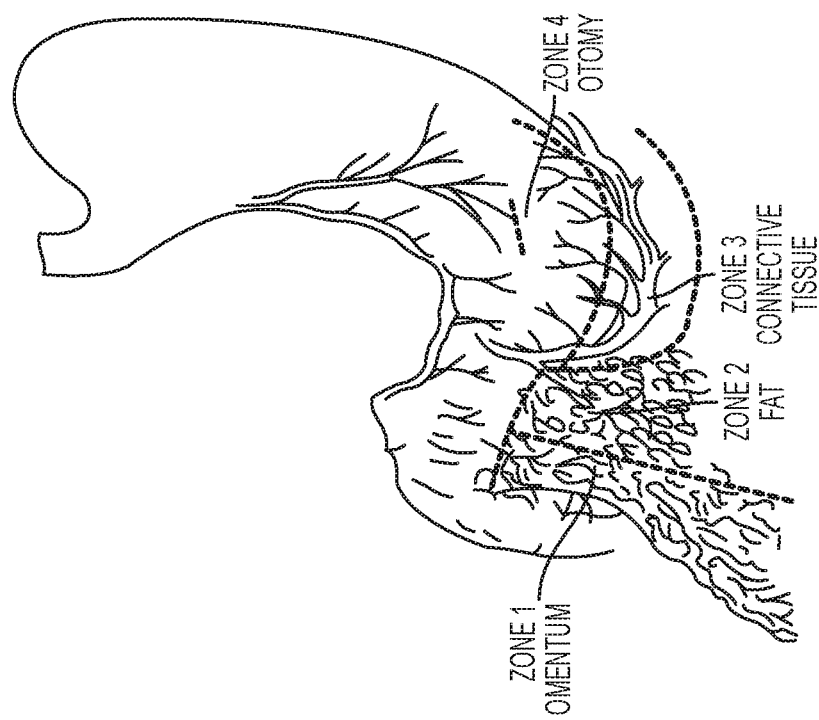
FIG. 6A is an exemplary schematic of a human stomach, showing different types of surrounding tissue.

As discussed above, once the cutting blade is inserted into tissue, the control system actuates the robotic arm to laterally move the cutting blade through the tissue at a treatment velocity thereby cutting tissue. A person of skilled art will appreciate that the cutting blade can encounter various types of tissue, e.g., as shown in FIG. 6A, and that for each type of tissue, a different amount of force should be applied to the cutting blade to allow the cutting blade to cut through the tissue, e.g., as shown in FIG. 6B. Unlike manually-operated devices, electrically-powered or automated surgical devices can lack control and tactile feedback when cutting through tissue, thereby increasing the risk of inadvertently cutting through certain tissue. Further the lack of control and tactical feedback can lead to a jam if the end effector encounters a different type of tissue and the device is not being operated at a power level sufficient to impart a force on the end effector that is needed to cut through the different type of tissue.

Accordingly various embodiments of control systems are provided for producing real-time feedback during the operation of electrically-power surgical devices so as to enable a user or robot to determine when the cutting blade has encountered a different type of tissue and control advancement of the cutting blade into the different types of tissue(s), if desired such advancement. In general, once the end effector is inserted into tissue, the control system can be configured to determine a tissue type by measuring a force acting upon the end effector when the end effector is moving through the tissue and measuring a tissue impedance encountered by the end effector during movement through the tissue. The control system can also be configured to require an affirmation by an operator that transition to a different type is desired.

Generally, as discussed above, the control system can control movement and actuation of a surgical device. For example, the control system can include at least one computer and can be operably coupled to the electromechanical tool and to motor that drives movement of the end effector through tissue at an insertion velocity. In certain embodiments, the control system can be a closed-loop feedback system. The stored data within the computer system can include predetermined thresholds for specific tissue types, such as predetermined force and impedance thresholds. When the control system is actuated, it drives one or more motors on or coupled to the surgical device, consequently actuating the drive assembly to insert the end effector into tissue. Once the end effector is inserted into tissue, the control system actuates the robotic arm to laterally move the end effector through the tissue at a treatment velocity thereby cutting tissue. During lateral movement, the control system can receive feedback input from one or more sensors coupled to the motor on the robotic arm to sense the motor force and one or more sensors coupled to the end effector to sense the tissue impedance being encountered by the end effector. If at any time during lateral movement, the control system determines that the received force input exceeds a predetermined force threshold and/or determines that the received tissue impedance input is less than a predetermined impedance threshold, the control system can modify the output data sent to the motor on the robotic arm based on the programmed logic functions.

For example, as shown in FIG. 6B, for each tissue type there can be a range for force (F) acting on the end effector and a range for tissue impedance (Z) encountered by the end effector during operation. As shown in FIGS. 6A-6B, there are four zones for four different types of tissue. Further, as shown in FIG. 6B, there is predetermined force thresholds, $F_1$ and $F_2$, in which the predetermined force threshold $F_1$ is for zone 1, whereas the predetermined force threshold $F_2$ is for zones 2 and 3. In FIG. 6B there are also predetermined impedance thresholds, $Z_A$ and $Z_B$, in which the predetermined impedance threshold $Z_A$ is for zone 1, whereas the predetermined impedance threshold $Z_B$ is for zone 2. These predetermined thresholds are stored as data in the computer system. While the control system can be designed to control various operations, in this exemplary embodiment, the control system actuates the motor on the robotic arm to drive lateral movement of the end effector while also determining the tissue type as the end effector is advancing there through.

In use, as the end effector is being advanced through a tissue type, the force acting upon the end effector and the tissue impedance being encountered by the end effector is measured and provided to the control system. At the same time, the control system compares the determined force and the determined tissue impedance against the predetermined thresholds to determine whether the end effector has reached a different type of tissue. For example, as shown in FIG. 6B, when the end effector is inserted into zone 1 and advanced there through, the force is less than the predetermined force threshold $F_1$ and the tissue impedance is greater than the predetermined impedance threshold $Z_A$. If at any time the control system determines that the measured force is greater than the predetermined force threshold $F_1$ and the measured tissue impedance is less than the predetermined impedance threshold $Z_A$, the end effector has therefore encountered a different tissue type, such as zone 2 or zone 3, and the control can then cease power delivery to the motor unless the control system receives affirmation from an operator that transition to the different tissue type is desired. If the control system receives affirmation, the control system can then increase the power to the motor so that the end effector can advance through the different type of tissue.

ii. Two or More Blades

In certain aspects, the surgical systems for cutting tissue can include an electromechanical tool having a housing and an instrument shaft that extends therefrom with an end effector at a distal end of the shaft, an actuator rod operably coupled to the end effector and extending through the shaft, a motor operably coupled to the actuator rod and configured to actuate the actuator rod, and a control system. In some aspects, the motor as well as the control system can be disposed within the housing, or can be located outside the housing, such as within a surgical robotic system.

While the end effector can include a variety of configurations for cutting tissue, in some implementations, the end effector can include a pair of cutting blades. In one embodiment, the cutting blades have sharpened cutting surfaces that face each other, as shown in FIGS. 7A-8B. It is also contemplated that in some embodiments, the cutting blades are initially dull, and when one cutting blade is energized, e.g., by a generator, it becomes sufficiently sharp to cut tissue.

As indicated above, in an exemplary embodiment control systems are provided for controlling actuation and movement of a surgical device. FIGS. 7A-8B illustrate one embodiment of a conventional surgical cutting device 400 for use with a control system. As shown, the device 400 has a handle housing 402, an instrument shaft 404 extending from the handle housing 402, and an end effector 406 attached to the distal end 404d of the instrument shaft 404. A moveable trigger 408 is operably connected to the end effector 406 and can facilitate closing and opening of the end effector 406. As shown, the end effector 406 is a single pair of scissors blades having first and second cutting blades 406a and 406b. A rotation knob 410 is provided to rotate the instrument shaft 404 and the first and second cutting blades 406a and 406b.

Figure 7A:
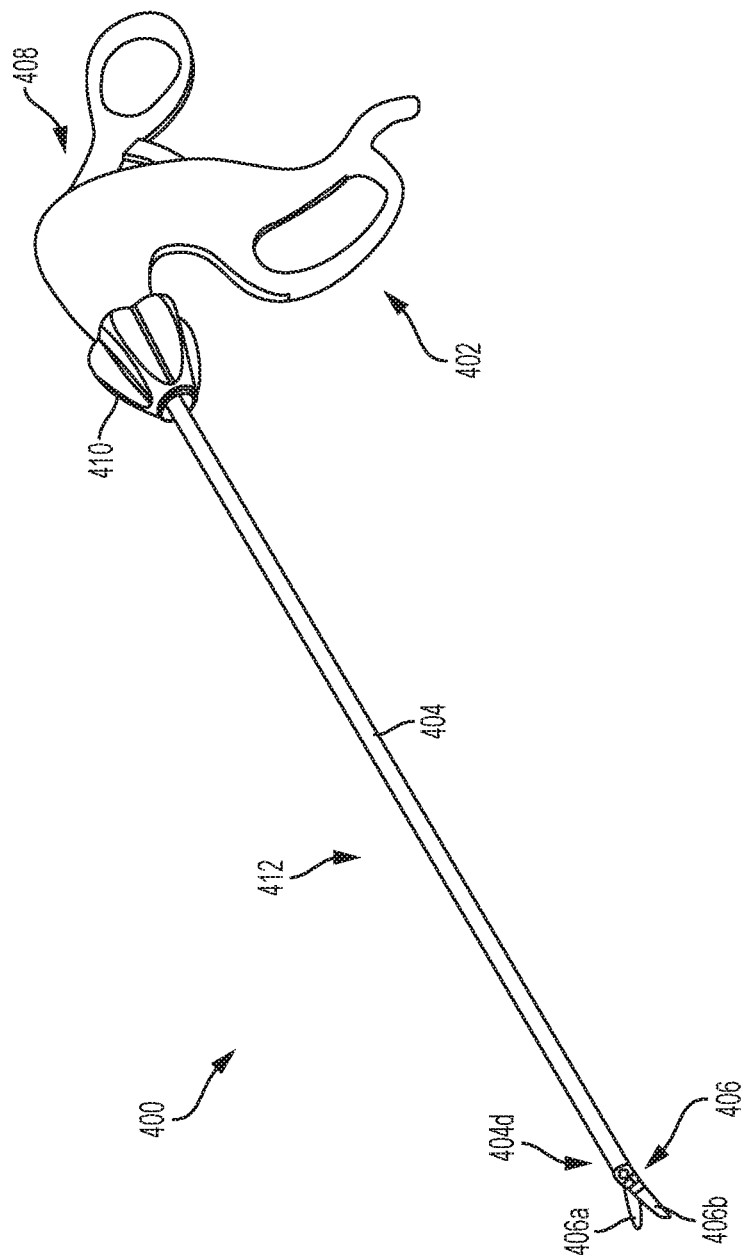
FIG. 7A is a side view of another exemplary embodiment of a surgical cutting device having two cutting blades in a partially opened configuration.
Figure 8A:
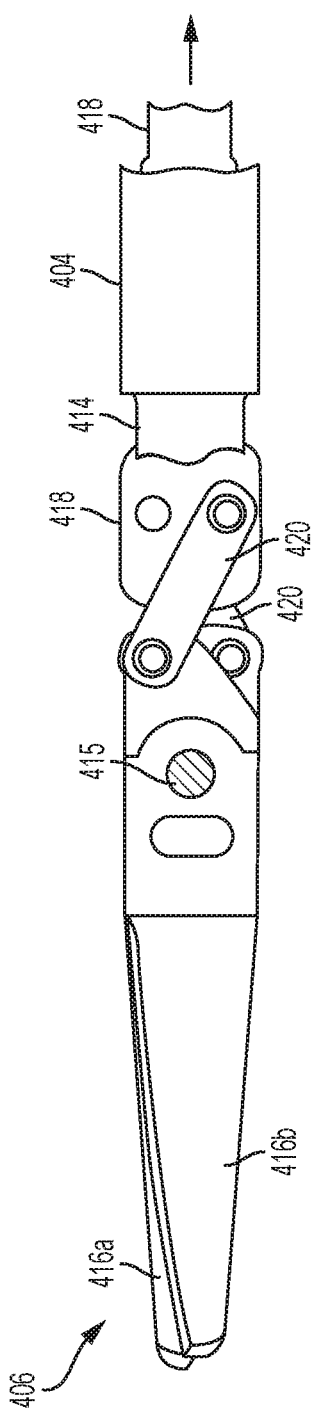
FIG. 8A is a side view of the distal portion of the surgical cutting device of FIG. 7A, showing the two cutting blades in a closed configuration.
Figure 8B:
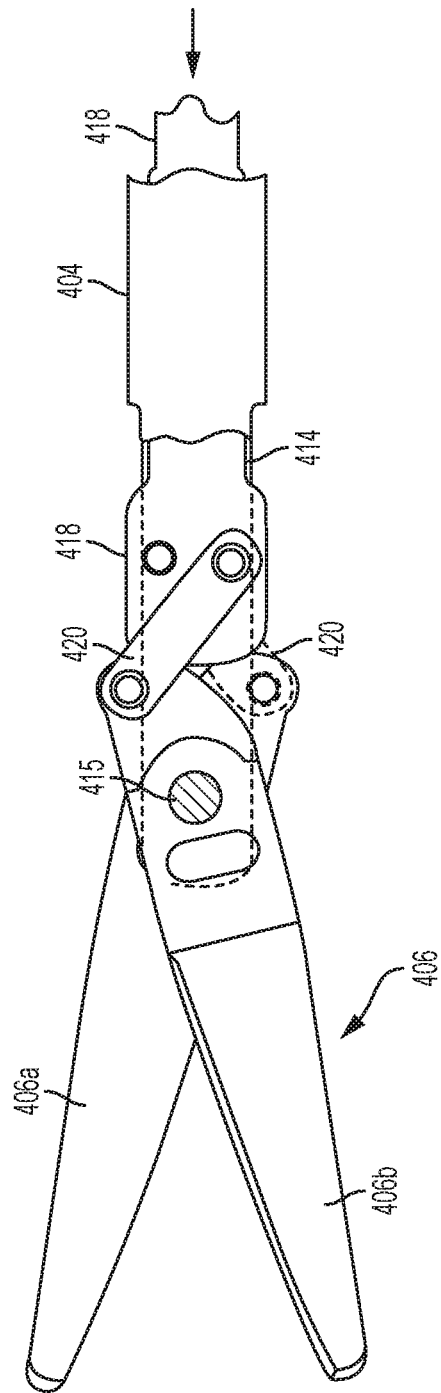
FIG. 8B is a side view of the distal portion of the surgical cutting device of FIG. 7A, showing the two cutting blades in a fully opened configuration.

As shown in FIG. 7B, the first and second cutting blades 406a and 406b are shown partially opened and mounted within a clevis 414. A first cutting edge 416a and an opposing second cutting edge 416b are located on the inside of first and second blades 406a and 406b, respectively. First and second cutting blades 406a and 406b rotate or pivot about a pivot member 415 that is perpendicular to a longitudinal axis L of the surgical cutting device 400. An actuation rod 418 is coaxially located and moveable within instrument shaft 404 and is operably connected to a pair of links 420 of the end effector 406. The instrument shaft 404, the end effector 406, and the actuator rod 418 are collectively referred to herein as an instrument shaft assembly 412. The links 420 operably connect the actuation rod 418 to the blades 406a and 406b such that distal and proximal motion of the actuation rod 418 open and close the blades 406a and 406b. In use, the actuation of the moveable trigger 408, allows the actuation rod 418 to move proximally, thereby pulling on the links 420 to close the blades 406a, 406b (FIG. 8A). When the desired cut is complete, the trigger 408 is released, thereby distally moving the actuator rod 418 to its initial position and consequently, opening of the blades 406a, 406b (FIG. 8B).

Exemplary embodiments and further details on surgical scissor devices, such as the conventional surgical cutting device above, are disclosed in U.S. Pat. No. 6,168,605 and in U.S. Patent Application No. 2016/0175060, each of which is incorporated by reference herein in its entirety.

As discussed above, a user applies manual force to the trigger 408 in order to drive the actuator rod 418 so as to move the cutting blades 406a, 406b between open and closed configurations. As such, the surgical cutting device 400, as illustrated in FIGS. 7A-7B, is a manually-operated device. However, more and more surgical procedures are being performed using electrically-powered surgical devices that are either hand-held or that are coupled to a surgical robotic system. Unlike manually-operated devices, electrically-powered surgical devices can lack control and tactile feedback, thereby reducing a surgeon's ability to effectively, accurately, and safely use these devices, for example, the ability to determine when a cut is complete.

Accordingly various embodiments of drive and control systems are provided for producing real-time feedback during the operation of electrically-powered surgical devices so as to enable a surgeon or other user to effectively and accurately use such devices. In general, the drive system is operably coupled to the instrument shaft assembly and to at least one motor that is configured to drive the actuator rod, and the control system is operably coupled to the at least one motor and is configured to actuate the at least motor to drive the drive system and thereby control movement of the actuator rod and consequently, the opening and closing of the jaws.

As indicated above, the motors as well as the control system can be disposed within the handle housing, like housing 402 shown in FIG. 7A, or can be located outside of the handle housing, such as within a surgical robotic system. Over the years a variety of minimally invasive robotic (or "telesurgical") systems have been developed to increase surgical dexterity as well as to permit a surgeon to operate on a patient in an intuitive manner. Many of such systems are disclosed in the following previously mentioned U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,132,368, entitled "Multi-Component Telepresence System and Method", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S.

Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Wristed Monopolar Electrosurgical End Effectors". Many of such systems, however, have in the past been unable to generate the magnitude of forces required to effectively cut and fasten tissue.

Figure 9A:
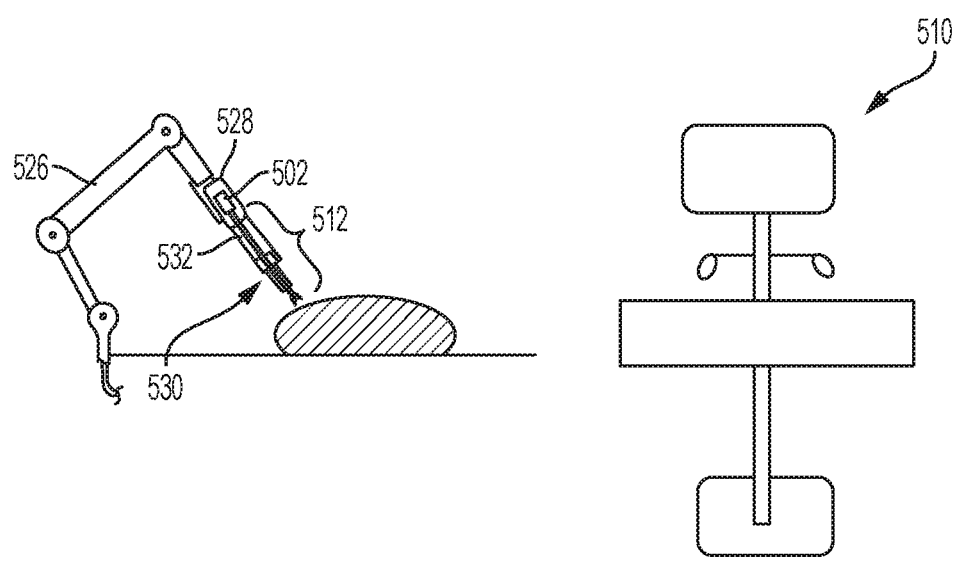
FIG. 9A is a perspective view of an exemplary embodiment of a surgical robotic system that includes a robotic arm having a drive system mounted in a motor housing on an end of the robotic arm, and being wirelessly coupled to a control system.

For example, FIG. 9A illustrates a robotic arm 526 wirelessly coupled to a control system 510 having a console with a display and two user input devices. One or more motors (not shown) are disposed within a motor housing 528 that is coupled to an end of the robotic arm 526. A tool or drive system housing 502 on a surgical tool can house a drive system (not shown) and it can be mounted to the motor housing 528 to thereby operably couple the motor(s) to the drive system. As a result, when the motors are activated by the control system, the motor(s) can actuate the drive system. As shown in FIG. 9A, an instrument shaft assembly 512 extends from the tool housing 502. During surgery, the instrument shaft assembly 512 can be placed within and extend through a trocar 536 that is mounted on the bottom of a carrier 532 extending between the motor housing 528 and a trocar support. The carrier 532 allows the tool to be translated into and out of the trocar 530. The robotic arm 526 is configured to support and move the electromechanical tool instrument shaft assembly 512 along one or more degrees of freedom (e.g., all six Cartesian degrees of freedom, five or fewer Cartesian degrees of freedom, etc.).

Exemplary embodiments of motor operation and components of a tool or drive system housing (also referred to as a "puck") configured to be controlled by motors are further described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, which is hereby incorporated by reference in its entirety.

Various wireless communication embodiments are described in U.S. patent application Ser. No. 13/118,259 to James R. Giordano et al. filed on May 27, 2011, the disclosure of which is herein incorporated by reference in its entirety.

Figure 9B:
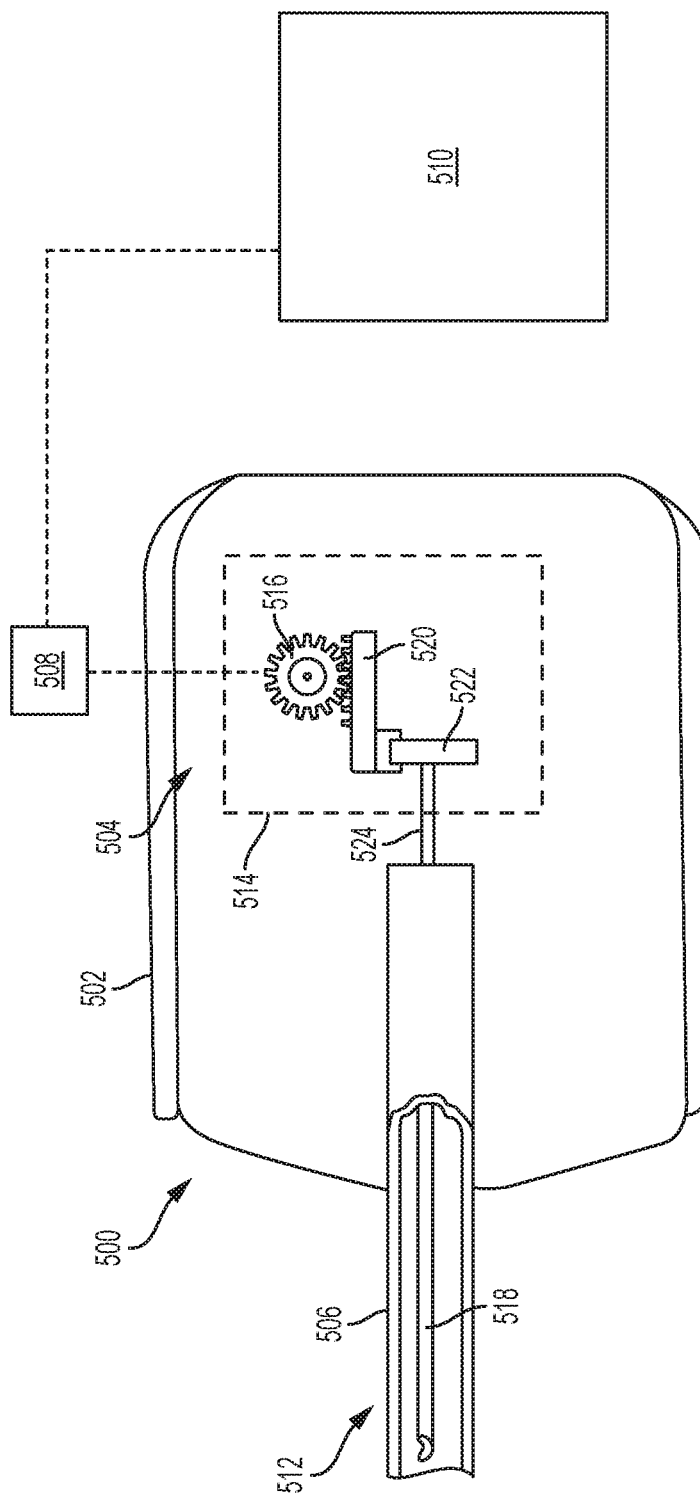
FIG. 9B is a side, partially transparent schematic view of an exemplary surgical cutting system having an actuator drive assembly that is coupled to a drive system, the drive system being coupled to a motor that is operably coupled to a control system.

FIG. 9B illustrates an exemplary embodiment of a surgical cutting system 500 having a tool housing 502 containing a drive system 504 and being coupled to a proximal end 506p of an instrument shaft 506 of an instrument shaft assembly 512. The drive system 504 is shown coupled to a motor 508 that is operably coupled to a control system 510. A person skilled in the art will appreciate that the motor(s) and control system can be located within the tool housing 502 to form a powered hand-held device, or they can be located external of the housing 502, such as in a robotic system as described with respect to FIG. 9A. Moreover, aside from the differences described in detail below, the instrument shaft assembly 512 can be similar to instrument shaft assembly 412 of FIGS. 7A-8B and is therefore not described in detail herein. Further, for purposes of simplicity, certain components of the instrument shaft assembly 512 are not illustrated in FIG. 9B.

The drive system 504 can have a variety of configurations. For example, as shown in FIG. 9B, the drive system 504 includes an actuator drive assembly 514 configured to cause the actuator rod 518 to advance in distal and proximal directions relative to the housing 502. The actuator drive assembly 514, which is discussed in more detail below, can be coupled to a rotary motor shaft of a corresponding motor 508, which in the illustrated embodiment (FIG. 9A) is disposed in a tool housing 502 on the end of the robotic arm 526. During actuation, the motor 508 can actuate the actuator drive assembly 514. Further, the motor 508 can be coupled to a torque sensor that provides the control system 510 with information about the amount of force being applied to the motor 508 during blade closure. Exemplary motors for use with the systems disclosed herein are described, for example, in previously mentioned U.S. Pat. Nos. 9,445,816 and 9,585,658 and in U.S. Patent Publication Nos. 2012/0292367 and 2015/0209059, each of which is incorporated by reference herein in its entirety.

The actuator drive assembly 514 can have a variety of configurations. For example, as shown in FIG. 9B, the actuator drive assembly 514 can include a rotary drive gear 516 that is in meshing engagement with a rack 520 that is coupled to a drive bracket 522 having a drive shaft 524 extending therefrom and in contact with the proximal end of the actuator rod 518. The rotary drive gear 516 can be operably coupled to the motor 508. In use, when the motor 508 is activated by the control system 510 and its corresponding rotary motor shaft drives the rotation of the rotary drive gear 516, thereby causing linear movement of the actuator rod 518. It will be appreciated that the application of a rotary output motion from the motor 508 in one direction will result in the linear movement of the actuator rod 518 in a proximal direction to move the cutting blades from an open configuration to a closed configuration when inserted into tissue. Further, application of the rotary output motion in an opposite direction will result in the linear movement of the actuator rod 518 in a distal direction, thereby moving the cutting blades from the closed configuration to the open configuration.

In certain embodiments, the surgical cutting device 500 can be monopolar. For example, the tool housing 502 (or any other part of the device 500) can include an input for electrical energy. In one embodiment, this electrical energy can be used to energize at least one of the cutting blades to cause the cutting blade(s) to become sufficiently sharp to cut tissue. The electrical energy can received from a local or remote power source, such as an electrosurgical generator (ESU). The power source may be designed to provide a specified amount of electrical energy or current with a specified waveform to at least one of the cutting blades. The electrical energy can be carried over a wire or other electrical conductor through the instrument shaft to the cutting blade(s). In one embodiment, an electrode can be disposed on one of the cutting blades such that the electrical energy is delivered through the electrode to the tissue.

In one embodiment, the cutting blades are initially dull, and when energized, the cutting blades can use high density (highly focused) electrical energy to cut through tissue. As such, a user can grasp the tissue between the initially dull cutting blades and, after confirming the desired location, positioning, or tissue, may initiate the flow of electricity to one or both of the cutting blades, thereby sharpening the blade(s) and cutting through the intervening tissue.

As discussed above, the control system can control movement and actuation of a surgical device. In certain embodiments, the control system can be a closed-loop feedback system. The stored data within the computer system can include predetermined magnitude(s) associated with predetermined range(s) of blade closure during operation of the surgical system. When the control system is actuated, it drives one or more motors on or coupled to the surgical device, consequently actuating the actuator drive assembly to move the cutting blades. During operation, the control system can receive feedback input from one or more sensors coupled to the motor(s) that sense the torque of the motor(s). The computer system can aggregate the received feedback input(s), perform any necessary calculations, compare it to a predetermined magnitude for a predetermined range of blade closure, and provide output data to the motor(s). If at any time during operation the control system determines that the received input meets or exceeds the predetermined magnitude, the control system can modify the output data sent to the motor based on the programmed logic functions. For example, the control system can modify the output data sent to the motor(s) to stop the current being delivered to the motor to thereby stop movement of the motor(s), and consequently, cease blade closure.

A person skilled in the art will appreciate that, while control systems are shown and described in this section with respect to an actuator drive assembly configured for a scissor device, the control systems disclosed herein can be coupled to one or more drive assemblies that are configured for other surgical devices.

As shown in FIG. 9B, the control system 510, which includes at least one computer system, can be operably coupled (wired or wirelessly) to the motor 508 that drives the actuator drive assembly 514. As described above, in use, the motor 508 is actuated by the control system 510. As a result, the control system 510 can control the movement of the actuator rod 518, and consequently, the movement of the cutting blades. For example, the control system can actuate and control the motor to move the actuator rod a known distance. This known distance correlates to a predetermined range of blade closure of the cutting blades. During blade closure, the control system can concurrently receive real-time feedback data from a torque sensor on the motor. After the control system has determined that the actuator rod has moved the known distance, e.g., by receiving input data from a rotary encoder on the motor, indicating the end of the predetermined range of blade closure, the control system is configured to cease blade closure when the motor torque exhibits or exceeds a predetermined magnitude, $\tau_{MAX}$ shown in FIG. 10.

Figure 10:
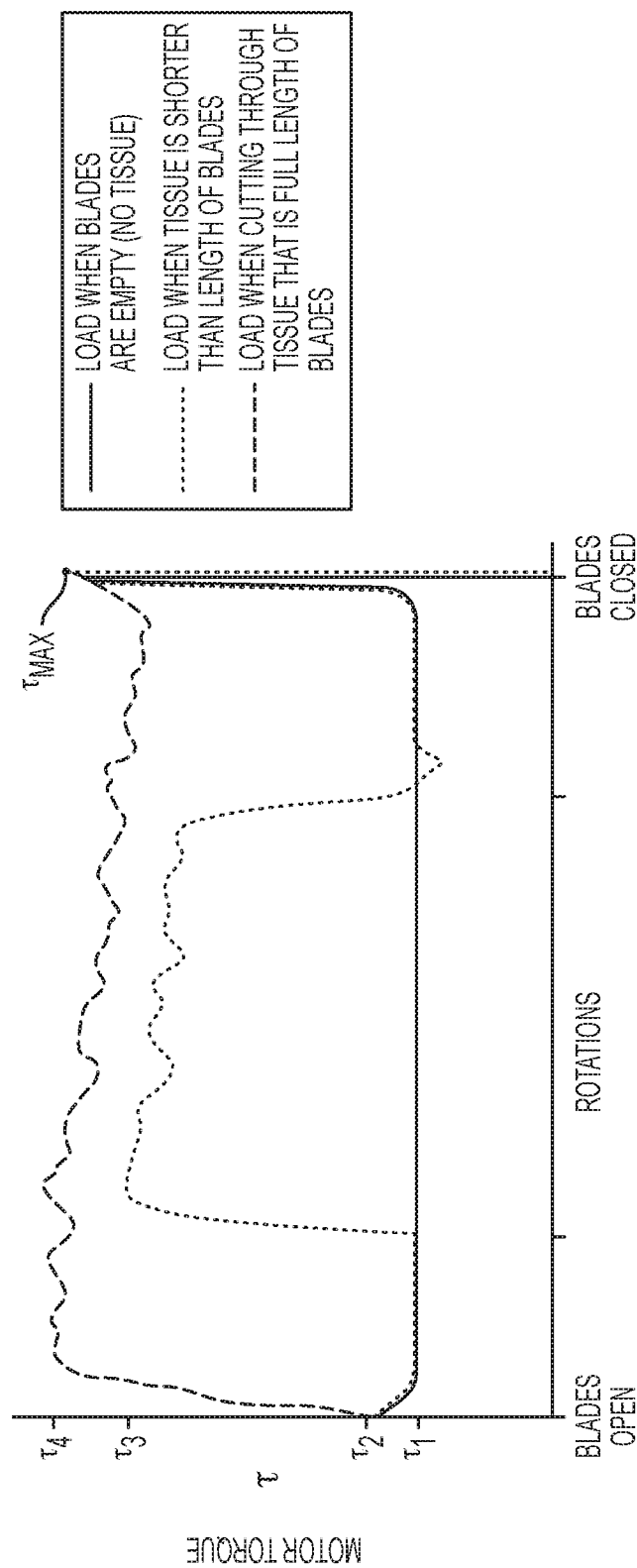
FIG. 10 is a graph illustrating the motor torque applied to the cutting blades of the surgical cutting device of FIG. 7A during blade closure.

In one embodiment, as shown in FIG. 10, when the cutting blades reach their closed configuration, an increase in torque occurs, indicated as the predetermined magnitude $\tau_{MAX}$. Thus, this predetermined magnitude $\tau_{MAX}$ correlates to complete cutting of tissue, and therefore meeting or exceeding this predetermined magnitude $\tau_{MAX}$ can be indicative of a tissue cut being completed, whereas failing to meet this predetermined magnitude $\tau_{MAX}$ can be indicative of a incomplete cut or jam due to, e.g., the tissue being too thick. Certain forces are required to move the cutting blades to a closed configuration during normal operation. The range of these forces can be determined during manufacturing, and therefore the predetermined magnitude $\tau_{MAX}$ can be determined based on the maximum torque that could be applied for properly cutting tissue, and consequently closing the cutting blades, during normal operation. As such, the control system's ability to cease blade closure based at least in part on reaching a predetermined magnitude thereby functions as the "tactile" feedback that would otherwise be experienced by a user of a manually-operated scissor device.

It should be noted that reaching or exceeding the predetermined magnitude can also be indicative of the sharpness of the cutting blades. For example, in one embodiment, when the motor torque exhibits the predetermined magnitude, as shown in FIG. 10, the cutting blades have reached their closed configuration. In order for the cutting blades to be moved from their open configuration to their closed configuration when cutting tissue, the cutting blades need to be of sufficient sharpness. As used herein, "sufficient sharpness" means a suitable sharpness for cutting through desired tissue. Thus, when the predetermined magnitude has been reached or exceeded, the cutting blades are determined to be of a sufficient sharpness. In other embodiments, even if the control system determines that the predetermined range of blade closure has been reached, if the motor torque fails to reach the predetermined magnitude, the cutting blades are determined to be of insufficient sharpness (dull), and consequently, the cut be incomplete and/or uneven.

B. Dissecting Devices

In general, the surgical systems described herein below are configured for dissecting tissue and include an electromechanical tool having an end effector with a pair of jaws, a motor, and a control system. While the control system can have a variety of configurations for each surgical system, the control system advantageously provides real-time feedback to a user or robotic system during surgery, so that the user or robotic system can determine the insertion depth of the electromechanical tool into tissue as well as the motor force during jaw opening. That is, the control system provides situational awareness to the user/robot, thereby allowing the user/robot to reduce or cease insertion and/or jaw opening of the electromechanical tool during surgery. For example, the control systems described herein can provide feedback to the user or robot during surgery to avoid applying excessive motor force to the end effector during jaw opening, thereby preventing damage to tissue and/or the device itself. Thus, the control systems enable a user or robot to know how fast the jaws can be opened based on motor force, as well as control jaw opening to allow for cauterizing tissue during otomy.

As indicated above, in an exemplary embodiment control systems are provided for controlling actuation and movement of a surgical dissecting device. FIGS. 11B-12B illustrate one embodiment of a conventional surgical dissecting device 600 for use with a control system. As shown, the device 600 can include a housing 602 having a stationary handle 604 and a trigger 606 in which the trigger 606 is configured to move relative to the housing 602. The device 600 also includes an instrument shaft assembly 608 extending therefrom. The instrument shaft assembly 608 includes an instrument shaft 610, an end effector 612 located at the distal end 610d of the instrument shaft 610, and an actuator 614 extending through the instrument shaft 610.

Figure 12B:
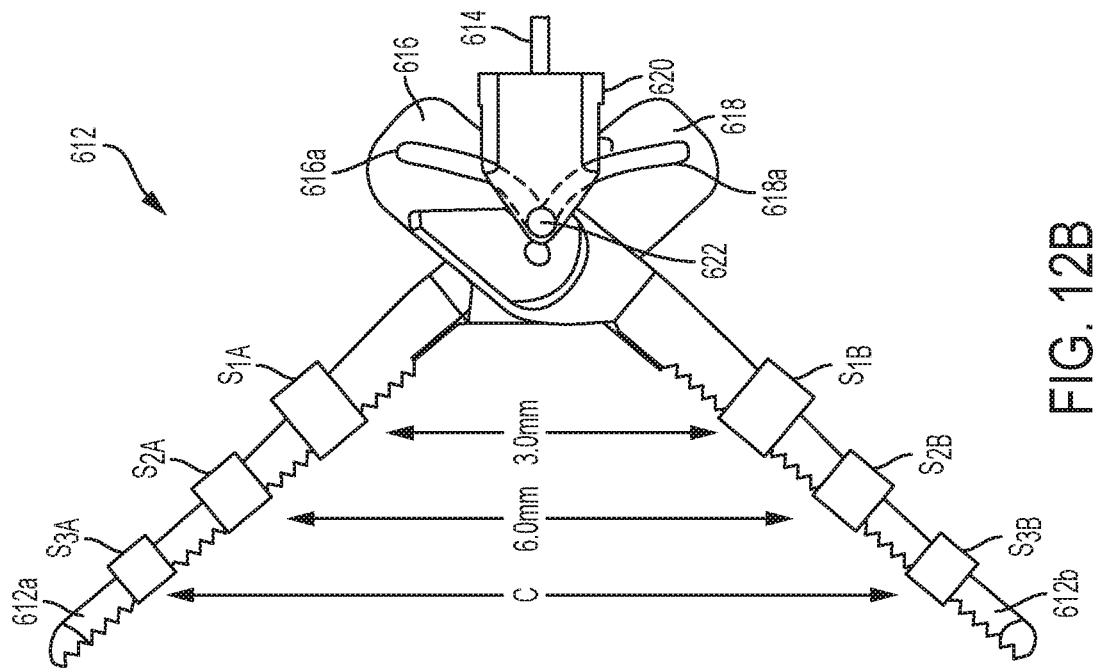
FIG. 12B is a side view of the distal portion of the surgical dissecting device of FIG. 11, showing the pair of jaws in an open configuration.
Figure 12A:
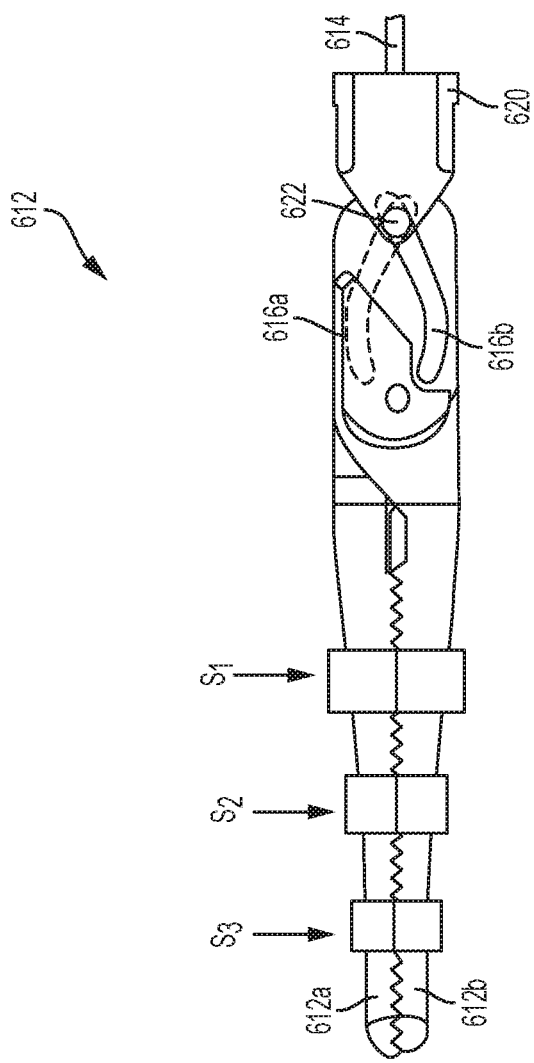
FIG. 12A is a side view of the distal portion of the surgical dissecting device of FIG. 11, showing the pair of jaws in a closed configuration.

As shown, an end effector 612 includes a pair of jaws 612a, 612b, which are shown in more detail in FIGS. 12A-12B. The jaws 612a, 612b are configured to selectively move from an open configuration to a closed configuration so as to engage and dissect tissue. The jaws include earn members 616, 618 that each define a cam slot 616a, 618a. The actuator 614 extends through the instrument shaft 610 and is operably coupled to a shuttle 620 that is to the engaged with the cam slots 616a, 618a via a pin 622. The actuator 612 is configured to selectively move the jaws 612a, 612b between the open configuration and the closed configuration.

In use, actuation of the trigger 606 allows the actuator 614 and the shuttle 620 to concurrently move in a proximal direction, thereby forcing the pin 622 to proximally slide within the cam slots 616a, 618a forcing the jaws 612a, 612b into a closed configuration (FIG. 12A). Once the desired tissue has been dissected, the trigger 606 is then released causing the actuator 614 and shuttle 620 to distally move to their initial position, and consequently, cause the pin 622 to distally slide to its initial position within the cam slots 616a, 618b thereby moving the jaws 612a, 612b from the closed configuration to the open configuration (FIG. 12B).

Additional details on dissecting surgical jaws, such as the conventional surgical dissection device described above, are disclosed in U.S. Patent Publication Nos. 2010/0198248 and 2017/0056038, each of which is incorporated herein by reference in its entirety.

Figure 11:
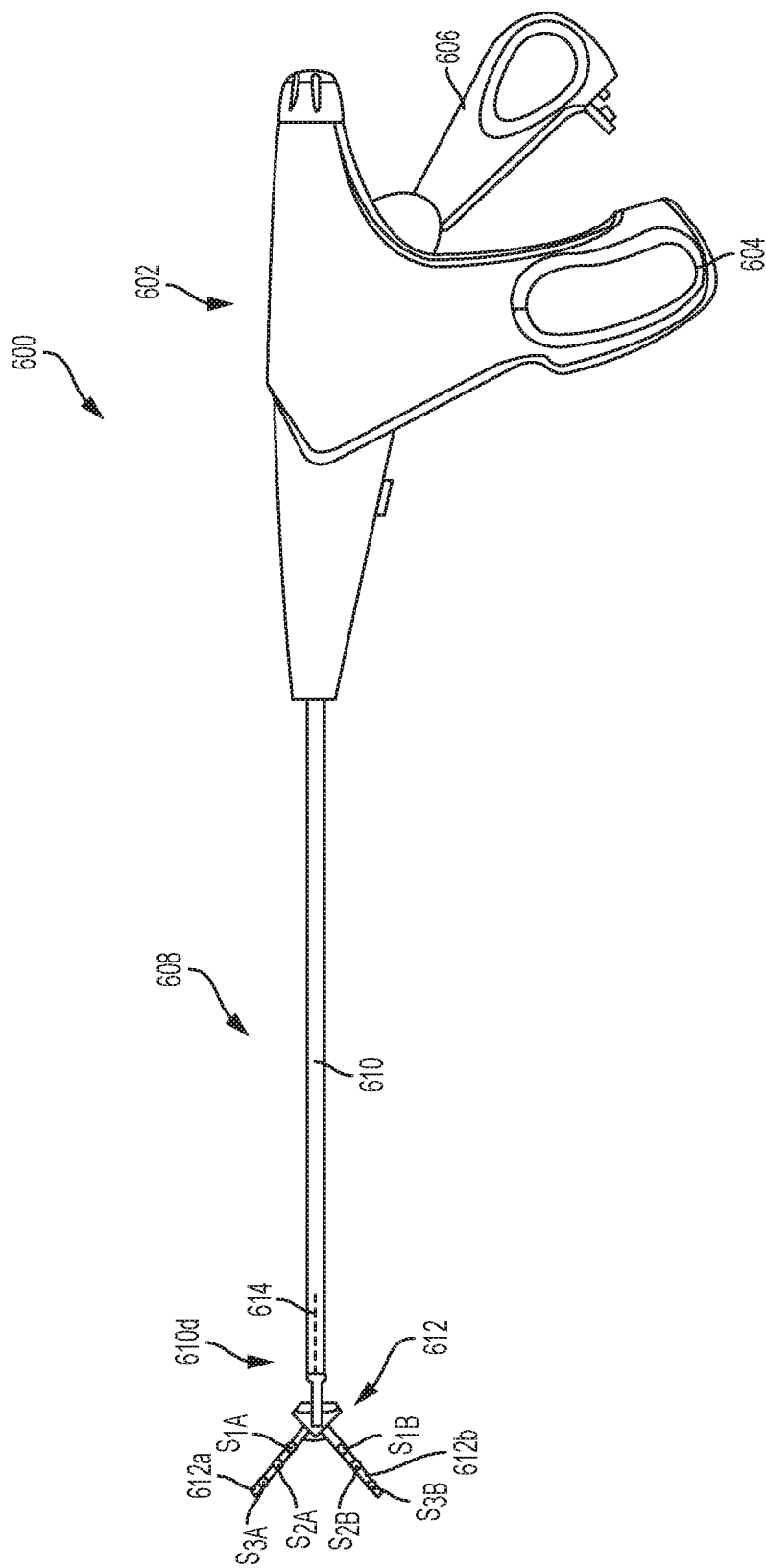
FIG. 11 is a side view of exemplary embodiment of a surgical dissecting device having a pair of jaws.

As discussed above, a user applies manual force to the trigger 606 in order to move the actuator 614 so as to move the jaws 612a, 612b between open and closed configurations. As such, the surgical dissector 600, as illustrated in FIGS. 11-12B, is a manually-operated device. However, more and more surgical procedures are being performed using electrically-powered surgical devices that are either hand-held or that are coupled to a surgical robotic system. Unlike manually-operated devices, electrically-powered surgical devices can lack control and tactile feedback, thereby reducing a surgeon's ability to effectively, accurately, and safely use these devices. Further, the insertion depth of jaws of manually-operated devices is typically determined visually and the jaw opening is velocity controlled (i.e., how fast the user actuates and releases the trigger). However, with electrically-powered devices, the control of insertion depth and jaw opening can be compromised due to the lack of tactical feedback.

Accordingly various embodiments of drive and control systems are provided for producing real-time feedback during the operation of electrically-powered surgical devices so as to enable a surgeon or other user to effectively and accurately use such devices. In general, the drive system is operably coupled to the instrument shaft assembly and to at least one motor that is configured to drive the actuator, and the control system is operably coupled to the at least one motor and is configured to actuate the at least motor to drive the drive system and thereby control movement of the actuator, and consequently, the opening and closing of the jaws.

As indicated above, the motors as well as the control system can be disposed within the handle housing, like housing 602 shown in FIG. 11, or can be located outside of the handle housing, such as within a surgical robotic system.

Figure 13A:
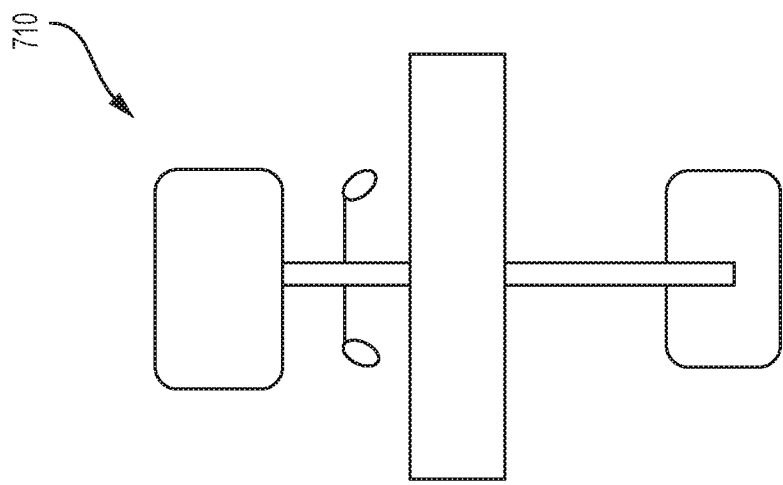
FIG. 13A is a perspective view of another exemplary embodiment of a surgical robotic system that includes a robotic arm having a drive system mounted in a motor housing on an end of the robotic arm, and being wirelessly coupled to a control system.
Figure 13A:
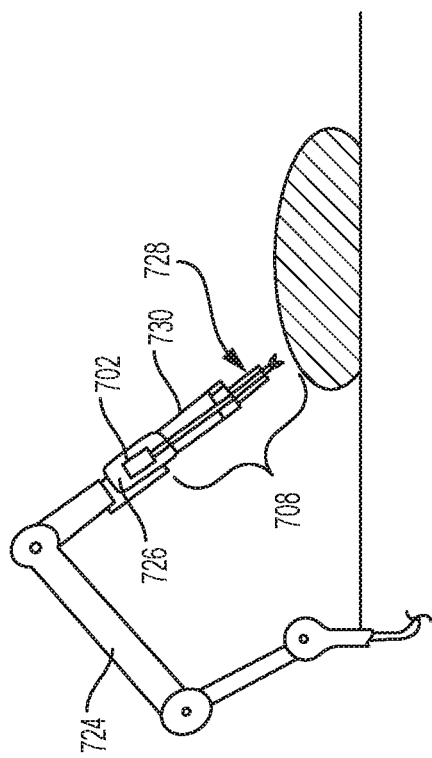

For example, FIG. 13A illustrates a robotic arm 724 wirelessly coupled to a control system 710 having a console with a display and two user input devices. One or more motors (not shown) are disposed within a motor housing 726 that is coupled to an end of the robotic arm 724. A tool or drive system housing 702 on a surgical tool can house a drive system (not shown) and it can be mounted to the motor housing 726 to thereby operably couple the motor(s) to the drive system. As a result, when the motors are activated by the control system 710, the motor(s) can actuate the drive system. As shown in FIG. 13A, an instrument shaft assembly 708 extends from the tool housing 702. During surgery, the instrument shaft assembly 708 can be placed within and extend through a trocar 728 that is mounted on the bottom of a carrier 730 extending between the motor housing 726 and a trocar support. The carrier 730 allows the tool to be translated into and out of the trocar 259. The robotic arm 724 is configured to support and move the instrument shaft assembly 708 along one or more degrees of freedom (e.g., all six Cartesian degrees of freedom, five or fewer Cartesian degrees of freedom, etc.).

Various wireless communication embodiments are described in previously mentioned U.S. patent application Ser. No. 13/118,259 to James R. Giordano et al. filed on May 27, 2011, the disclosure of which is herein incorporated by reference in its entirety.

Figure 13B:
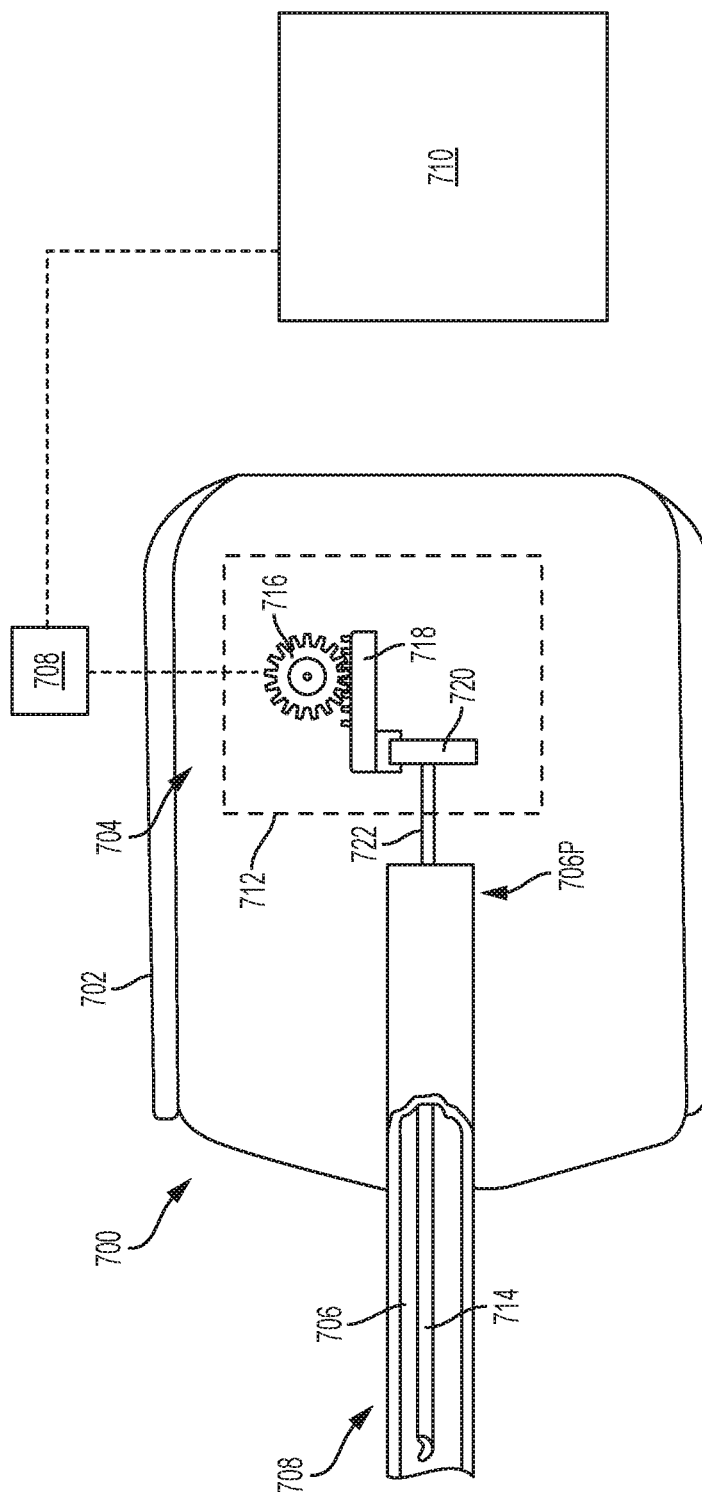
FIG. 13B is a side, partially transparent schematic view of an exemplary surgical dissecting system having an actuator drive assembly that is coupled to a drive system, the drive system being coupled to a motor that is operably coupled to a control system.

FIG. 13B illustrates an exemplary embodiment of surgical dissecting system 700 having a tool housing 702 containing a drive system 704 and being coupled to a proximal end 706p of an instrument shaft 706 of an instrument shaft assembly 708. The drive system 704 is shown coupled to a motor 708 that is operably coupled to a control system 710. A person skilled in the art will appreciate that the motor(s) and control system can be located within the tool housing 702 to form a powered hand-held device, or they can be located external of the housing 702, such as in a robotic system as described with respect to FIG. 13A. Moreover, aside from the differences described in detail below, the instrument shaft assembly 708 can be similar to instrument shaft assembly 608 of FIGS. 11-12B and is therefore not described in detail herein. Further, for purposes of simplicity, certain components of the instrument shaft assembly 708 are not illustrated in FIG. 13B.

In some embodiments, the pair of jaws, like jaws 612a, 612b as shown in FIGS. 11-12B, is monopolar. Exemplary embodiments and additional details on monopolar surgical dissecting devices are disclosed in U.S. Pat. Nos. 6,039,735, 6,066,137, 8,439,910, and 9,168,092 and in U.S. Patent Publication Nos. 2014/0005718 and 2017/0196637, each of which is incorporated herein by reference in its entirety.

The drive system 704 can have a variety of configurations. For example, as shown in FIG. 13B, the drive system 704 includes an actuator drive assembly 712 configured to cause the actuator 714 to advance in distal and proximal directions relative to the housing 702. The actuator drive assembly 712, which is discussed in more detail below, can be coupled to a rotary motor shaft of a corresponding motor 708, which in the illustrated embodiment (FIG. 13A) is disposed in a driving system housing 702 on the end of the robotic arm 724. During actuation, the motor 708 can actuate the actuator drive assembly 712. Further, the motor 708 can be coupled to a torque sensor that provides the control system 710 with information about the amount of force being applied to the motor 708 during jaw opening and jaw closing. Exemplary motors for use with the systems disclosed herein are described, for example, in previously mentioned in U.S. Pat. Nos. 9,445,816 and 9,585,658 and in U.S. Patent Publication Nos. 2012/0292367 and 2015/0209059, each of which is incorporated by reference herein in its entirety.

The actuator drive assembly 712 can have a variety of configurations. For example, as shown in FIG. 13B, the actuator drive assembly 712 can include a rotary drive gear 716 that is in meshing engagement with a rack 718 that is coupled to a drive bracket 720 having a drive shaft 722 extending therefrom and in contact with the proximal end of the actuator 714. The rotary drive gear 716 can be operably coupled to the motor 708. In use, when the motor 708 is activated by the control system 710 and its corresponding rotary motor shaft drives the rotation of the rotary drive gear 716, thereby causing linear movement of the actuator 714. It will be appreciated that the application of a rotary output motion from the motor 708 in one direction will result in the linear movement of the actuator 714 in a distal direction to move the jaws from an open configuration to a closed configuration when inserted into tissue. Further, application of the rotary output motion in an opposite direction will result in the linear movement of the actuator 714 in a proximal direction to retract the actuator 714 to move the jaws from the closed configuration to the open configuration when inserted into tissue.

Figure 14:
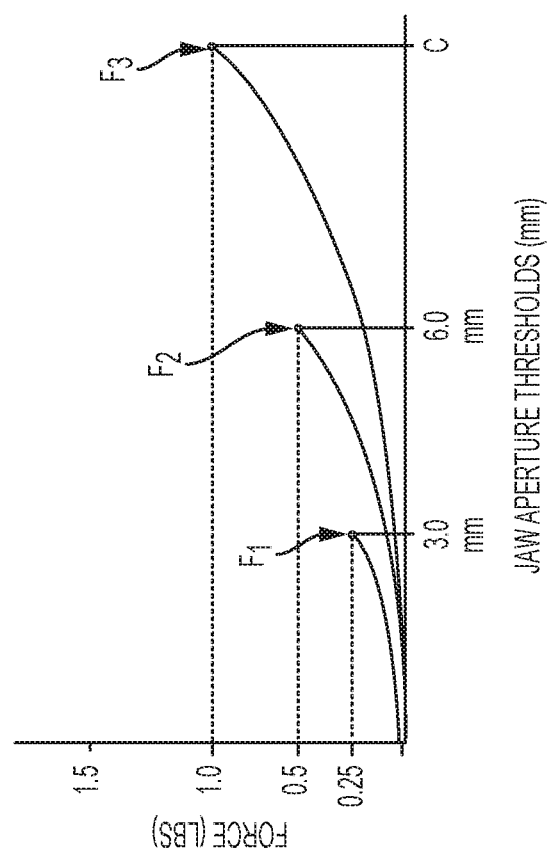
FIG. 14 is a graph illustrating predetermined thresholds at specific areas of the jaws shown in FIG. 11 for a known insertion depth.

In use, the jaws are typically inserted into the tissue in a closed configuration and when the jaws are at a desired insertion depth, they are moved to an open configuration. The insertion depth of the jaws can be determined by at least a pair of sensors located on the jaws. While one or more pair of sensors can be used and placed at various locations on the jaws, in one exemplary embodiment, as shown in FIGS. 11-12B, the jaws 612a, 612b include three pairs of sensors, $S_1$, $S_2$, $S_3$ that can determine tissue location of the jaws. Each pair of sensors can correspond to a jaw aperture threshold at a specific area of the jaw. For example, in FIG. 12B, the first pair of sensors $S_{1A}$, $S_{1B}$ correspond to a jaw aperture of 3.0 mm, the second pair of sensors $S_{2A}$, $S_{2B}$ correspond to a jaw aperture of 6.0 mm, and the third pair of sensors $S_{3A}$, $S_{3B}$ correspond to a jaw aperture C. Each sensor can be operably coupled, e.g., wirelessly, to the control system so as to provide information about jaw location during insertion into tissue. As shown in FIG. 14, for each jaw aperture threshold, there is a corresponding predetermined motor force threshold, $F_1$, $F_2$, $F_3$, as discussed in more detail below in connection with the control system.

Generally, as discussed above, the control system can control movement and actuation of a surgical device. In certain embodiments, the control system can be a closed-loop feedback system. The stored data within the computer system can include predetermined motor threshold(s) for specific jaw apertures at one or more areas of the jaw. The predetermined motor force threshold(s) are also related to the insertion depth of the end effector. The greater the insertion depth, the greater the predetermined motor thresholds, $F_1$, $F_2$, $F_3$ for jaw opening. FIG. 14 illustrates the relationship between motor force thresholds and jaw aperture thresholds at specific areas of the jaw for a known insertion depth. When the control system is actuated, it inserts the jaws into tissue, e.g., by a robotic arm, at a specific insertion depth. The control system can verify the insertion depth using one or more sensors located on the jaws. During jaw opening, the control system can receive feedback input from one or more sensors on the motor that sense torque of the motor when the jaws are being opened at the determined insertion depth. In one embodiment, the computer system can aggregate the received feedback input(s), perform any necessary calculations, compare the sensed motor force to the predetermined motor force threshold at the determined insertion depth, and provide output data to the motor(s). Alternatively, or in addition, the computer system can compare the sensed motor force to the predetermined motor force threshold for a specific jaw aperture at the determined insertion depth, and provide output data to the motor(s).

Figure 15:
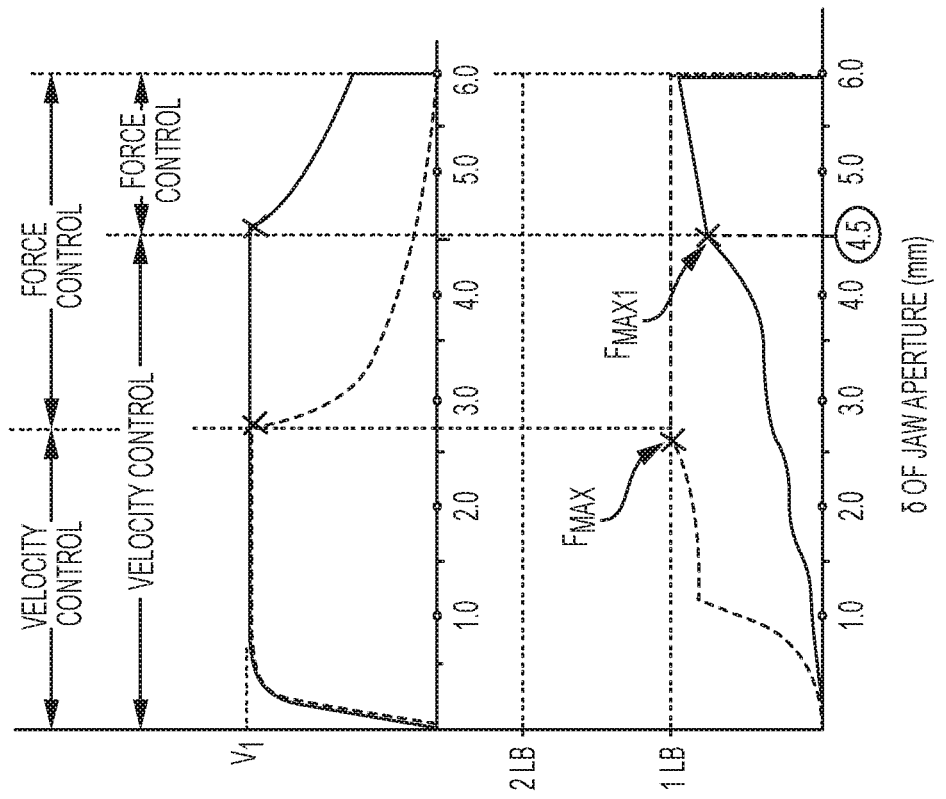
FIG. 15 is a graph illustrating a process for controlling the velocity and motor force being applied to the jaws shown in FIG. 11 during jaw opening at a specific insertion depth.

In one embodiment, the control system is configured to permit jaw opening at a predetermined velocity unless the motor force exceeds a predetermined motor force, $F_{MAX}$ as shown in FIG. 15, threshold corresponding to the determined insertion depth. That is, the control system can limit the force being used to open the jaws, and consequently the spreading (dissecting) of tissue. If at any time during jaw opening at a determined insertion depth the control system determines that the motor force reaches or exceeds a predetermined motor force threshold, e.g., $F_{MAX}$ in FIG. 15, the control system can modify the output data sent to the motor based on the programmed logic functions. For example, as shown in FIG. 15, the control system can modify the output data sent to the motor to thereby limit the motor force to the jaws after the predetermined motor force threshold $F_{MAX}$ has been reached so that the motor force does not exceed the predetermined motor force threshold $F_{MAX}$ as the jaws continue to open. Consequently, as shown in FIG. 15, when this occurs, the velocity at which the jaws open decreases. That is, while the initial jaw opening occurs at a predetermined velocity, and is therefore velocity controlled, if the motor force exceeds the predetermined motor threshold $F_{MAX}$ for the determined insertion depth, the jaw opening shifts to force-control. As a result, the opening of the jaws continues at a reduced velocity relative to the predetermined velocity.

In another embodiment, as shown in FIG. 15, the control system is configured to permit jaw opening at a predetermined velocity (i.e., the jaw opening is velocity-controlled) until the motor force reaches the predetermined motor force threshold corresponding to a specific jaw aperture at the determined insertion depth. As discussed above, the control system can therefore limit the force being used to open the jaws and consequently, the spreading (dissection) of tissue. Once the control system determines that the motor force has reached the predetermined motor threshold for the specific jaw aperture, e.g., $F_{MAX}$ at 4.5 mm jaw aperture in FIG. 15, the control system can modify the output data sent to the motor based on the programmed logic functions. For example, as shown in FIG. 15, the control system can modify the output data sent to the motor to thereby limit the motor force to the jaws once the predetermined motor force threshold, $F_{MAX}$, has been reached so that the jaws can continue to open to the max jaw aperture, e.g., 6.0 mm in FIG. 15, without exceeding the maximum motor force threshold, $F_{MAX}$ in FIG. 15, for the determined insertion depth. As a result, as shown in FIG. 15, when this occurs, the velocity at which the jaws open decreases. That is, while the initial jaw opening occurs at a predetermined velocity, and is therefore velocity-controlled, if the motor force reaches the predetermined motor threshold, e.g., $F_{MAX}$, for a specific jaw aperture, the opening of the jaws shifts to force-control. As a result, when the jaws are in force-control, the opening of the jaws continues at a reduced velocity relative to the predetermined velocity.

Typically, the jaws of dissecting devices are configured to open and close freely. As discussed above with respect to FIG. 13B, activation of the motor 708 causes proximal movement of the actuator (or actuator rod) 714 which in turn moves the jaws from an open configuration to a closed configuration. In certain instances, however, once tissue is positioned between the jaws, i.e., the jaws are in a closed configuration about tissue, it may be desirable to prevent the reopening of the jaws for a specific period of time so that a user or robot can manipulate and dissect the tissue without the tissue being prematurely released from the jaws. Thus, in certain embodiments, the control systems described herein can include an advancement lock mode in which the control system can be configured to control the rotary movement of the motor.

Figure 16:
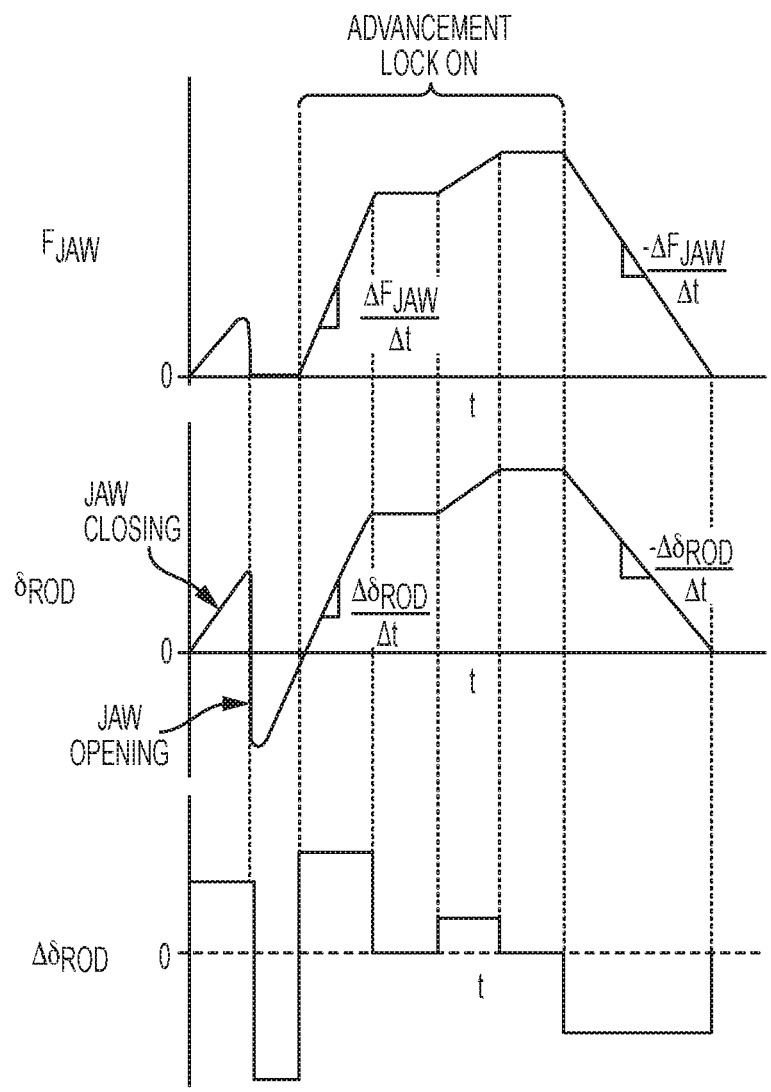
FIG. 16 is a graph illustrating a process for controlling the rotary movement of the motor shown to impart an advancement lock on the actuator drive assembly shown in FIG. 13B.

For example, as shown in FIG. 16, once the jaws have closed about tissue, a user or robot can actuate the advancement lock mode of the control system. Once the advancement lock mode has been activated by the user or robot, the control system is prompted to cease rotary movement of the motor, $\Delta\delta_{ROD}=0$, and/or allow only rotary movement that causes the actuator rod to move in a proximal direction, $\Delta\delta_{ROD}=0$. In this way, the jaws can either remain stationary, or if desired, can further close to grasp the tissue tighter between the jaws.

Zones of Avoidance

Monopolar electrosurgery can be used for several modalities including cutting, dissection, and cauterization. With monopolar electrosurgery, potential capacitive coupling can occur. Capacitive coupling is a mechanism whereby electrical current in the electrode disposed on the surgical device unintentionally induces a current in nearby conductive surgical devices despite otherwise intact insulation. While in certain instances this may be desirable, in other instances it is not and can lead to accidental damage to tissue, e.g., burning of tissue, outside the area of interest.

As indicated above, the surgical devices described herein can be monopolar devices. Once a surgical monopolar device is energized, an electrical field around the device is created, and to prevent capacitive coupling any conductive secondary electromechanical surgical devices should avoid this electrical field. As such, the electrical field is referred herein as the zone of avoidance. The control systems described herein below can be configured to avoid capacitive coupling during surgery. For example, the control system can be configured to determine the zone of avoidance surrounding an electromechanical tool when energy is delivered to tissue during surgery and prevent a secondary electromechanical tool from entering this zone.

Figure 17A:
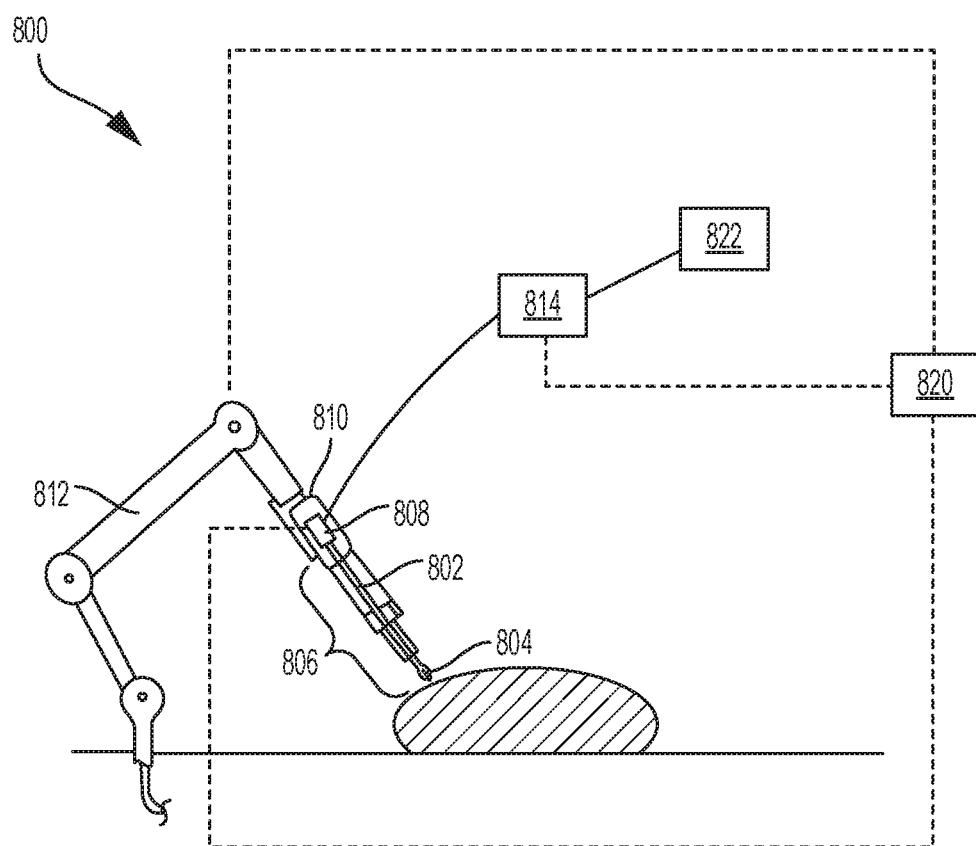
FIG. 17A is a perspective view of another exemplary embodiment of a surgical system that includes an electromechanical tool coupled to a generator and to a robotic arm in which the electromechanical tool, generator, and robotic are each wirelessly coupled to a control system.
Figure 17B:
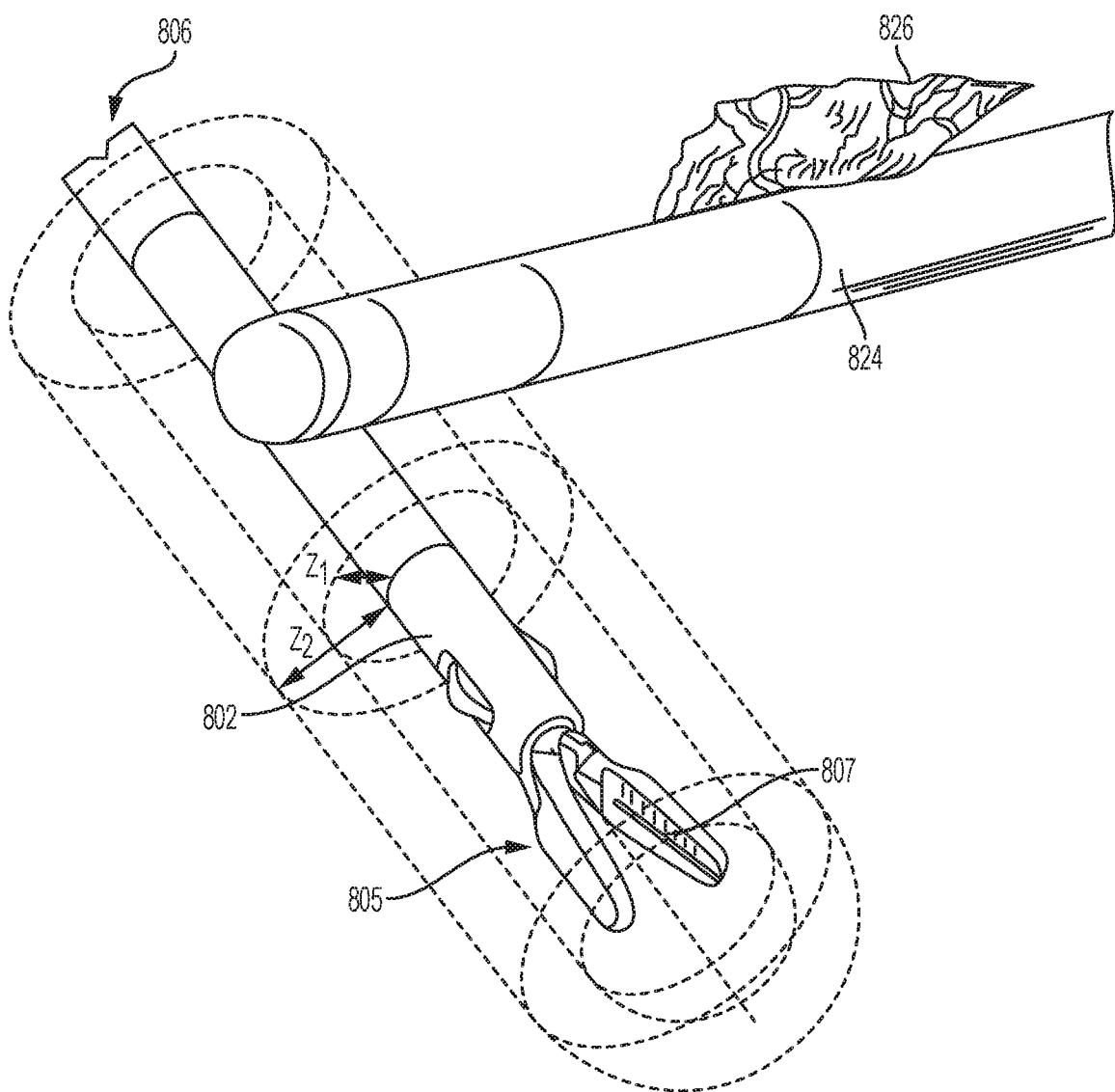
FIG. 17B is a perspective view of the electromechanical tool of FIG. 17A when energized, showing zones of avoidance with a secondary electromechanical tool located within these zones.

FIGS. 17A-17B is an exemplary embodiment of surgical system 800 having a monopolar electromechanical tool 806 that includes an instrument shaft 802 and an end effector 804, collectively the instrument shaft assembly. While the end effector 804 can have a variety of configurations, in this exemplary embodiment, the end effector 804 is a pair of jaws 805 having an electrode 807 disposed on one of the jaws. The instrument shaft assembly extends from a tool housing 808 that is mounted to a motor housing 810 that is coupled to the electromechanical arm 812. The electromechanical arm 812 can be configured to support and move the electromechanical tool 806 along one or more degrees of freedom (e.g., all six Cartesian degrees of freedom, five or fewer Cartesian degrees of freedom, etc.). For example, the electromechanical arm 812 can be configured to move, position and insert the end effector 802 into tissue.

As shown in FIG. 17A, the electromechanical tool 806 is operatively connected to a generator 814 to provide an off-board power source to power the electrode 807. Alternatively, an on-board power source can be used to power the electrode 807. In the illustrated embodiment, the generator 814 is a separate unit that is electrically connected to the tool housing 808. The generator 814 is also operatively coupled (wired or wirelessly) to the control system 820. A bore (not shown) of the instrument shaft 802 can carry electrical leads to wires that can deliver electrical energy from the generator 814 to the electrode 807. In FIG. 17A, a return electrode 822 is shown coupled (wired or wirelessly) to the generator 814. Before surgery, this return electrode 822 is placed on the patient.

The generator 814 can be any suitable generator known in the art that is configured to generate suitable types of signals for electrosurgical applications, such as an RF generator. Exemplary embodiments of generators are disclosed in U.S. Publication Nos. 2016/0089533, 2011/0087256, and 2011/0015631, each of which is incorporated by reference herein in its entirety.

The control system 820 is shown in FIG. 17A to be operably coupled to both the electromechanical tool 806 and arm 812 so that the control system 820 can control movement thereof, and also operably coupled to the generator 814. In use, the control system actuates the electromechanical arm, and consequently, the electromechanical tool for positioning and for insertion into tissue. Once the electromechanical tool is positioned at the desired location, at least the end effector of the electromechanical tool is inserted into the tissue. The control system then prompts the generator to deliver energy to the electrode in which the energy is then delivered through the electrode to tissue.

Typically, more than one electromechanical tool is used during surgery. In instances where the monopolar electromechanical tool 806 is being used, capacitive coupling to a conductive secondary electromechanical tool that is concurrently being used can occur. As stated above and illustrated in FIG. 17B, when the monopolar electromechanical tool 806 is energized, an electrical field, also referred herein to as a zone of avoidance, $Z_1$ and $Z_2$, is created around the tool 806. As shown in FIG. 17B, if a conductive secondary electromechanical tool 824 enters the zone of avoidance, inadvertent burning of non-target tissue 826 can occur.

Accordingly various embodiments of control systems are provided for preventing a conductive secondary electromechanical tool from entering a zone of avoidance of a monopolar electromechanical tool. Thus, in addition to being configured to control movement of the electromechanical arm and tool, the control system can also be configured to determine a zone of avoidance (Z) of the electromechanical tool when energy is being delivered to the tissue through the electrode, and either reduce the zone of avoidance and/or redirect the conductive secondary electromechanical tool away from the zone of avoidance.

In certain embodiments, the control system can be a closed-loop feedback system. The stored data within the computer system can include predetermined zone of avoidances. When the control system is actuated, the electrode is energized and the control system determines the zone of avoidance for the power level at which the electromechanical tool is being operated. For each power level, there is a zone of avoidance. During operation, the control system can receive feedback input from the robot that relates to a first energy level of a secondary electromechanical tool relative to a second energy level (e.g., ground) such that the control system can thereby determine when entry of the secondary electrochemical tool into the zone of avoidance is imminent. For example, the robot can be configured to calculate the energy flowing through the secondary electromechanical tool based at least in part on the impedance of the tissue being encountered and the power level at which the electromechanical tool is being operated, and transmit this calculated data to the control system. Alternatively, or in addition to, the control system can also receive feedback input relating to a distance of the secondary electromechanical tool relative to the determined zone of avoidance. In some embodiments, the feedback input can be provided by the robot, e.g., by kinematic calculation of the robot joints and actuation positions or by using the robot stereo vision optics which allows it to determine distances within the field of view and it could calculate the proximity of one instrument to the next. In other embodiments, the feedback input can be provided using a three-dimensional magnetic field sensor on each electromechanical tool which would not only allow the control system to detect true position of the tools with respect to the base field transmitter, but orientation as well.

The computer system can aggregate the received feedback input(s), perform any necessary calculations, compare it to the determined zone of avoidance for the corresponding power level, and provide output data to the motor(s). If at any time during operation the control system determines that entry into the zone of avoidance by the secondary electromechanical tool is imminent, the control system can modify the output data sent to the generator or the output data sent to the motor of the electromechanical arm based on the programmed logic functions. For example, the control system can modify the output data sent to the generator to reduce current being delivered to the electrode. Alternatively or in addition, the control system can modify the output data sent to a motor of the electromechanical arm to redirect the secondary electromechanical tool.

Figure 18:
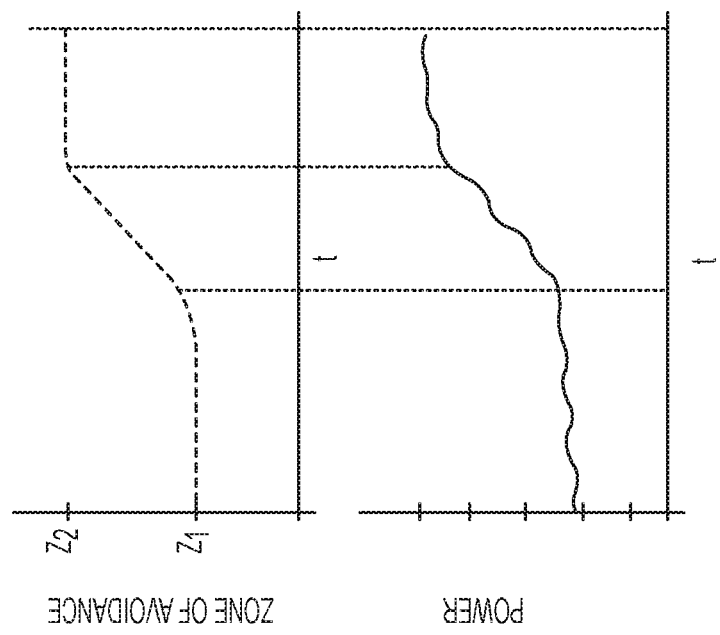
FIG. 18 is a graph illustrating the relationship between the zone of avoidance of an energized electromechanical tool and the power at which energy is being delivered to tissue by the energized electromechanical tool.
Figure 19:
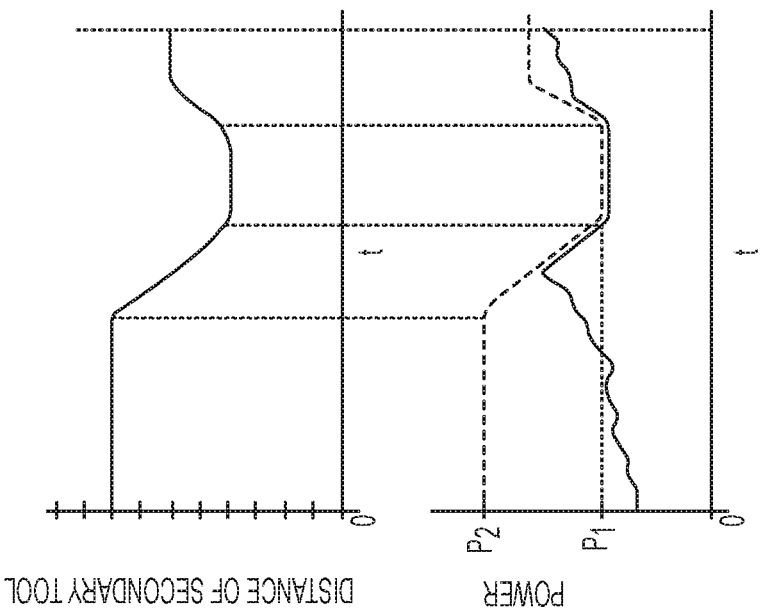
FIG. 19 is a graph illustrating the relationship between the distance of the secondary electromechanical tool and the power at which energy is being delivered to tissue by the energized primary electromechanical tool.

In FIG. 18, the relationship between the zone of avoidance (Z) and power is illustrated, and in FIG. 19, the relationship between power and the distance of the secondary electromechanical tool relative to the primary tool is illustrated. As shown, the zone of avoidance can be dependent at least on the power level at which energy is being delivered to tissue. That is, as the power level increases, the zone of avoidance increases, and vice versa (FIG. 18). Thus, in one embodiment, when the control system determines that entry of a secondary electromechanical tool into the zone of avoidance is imminent, the control system is configured to reduce the power level at which energy is being delivered to the tissue by the electrode. For example, the control system can be configured to control, and therefore modify, the current being applied to the electrode from the generator. As a result, when the power level is reduced, the size of the zone of avoidance is reduced and the reduced size is maintained, thereby preventing capacitive coupling between the electromechanical tool and the secondary electromechanical tool.

In other embodiments, the control system can prevent the secondary electromechanical tool from entering the zone of avoidance without modifying the size of the zone of avoidance. For example, in one embodiment, the control system can be operably coupled to the secondary electromechanical tool and configured to cease movement of the secondary electromechanical tool relative to the electromechanical tool or redirect the secondary electromechanical tool away from the zone of avoidance.

Computer Systems

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 20:
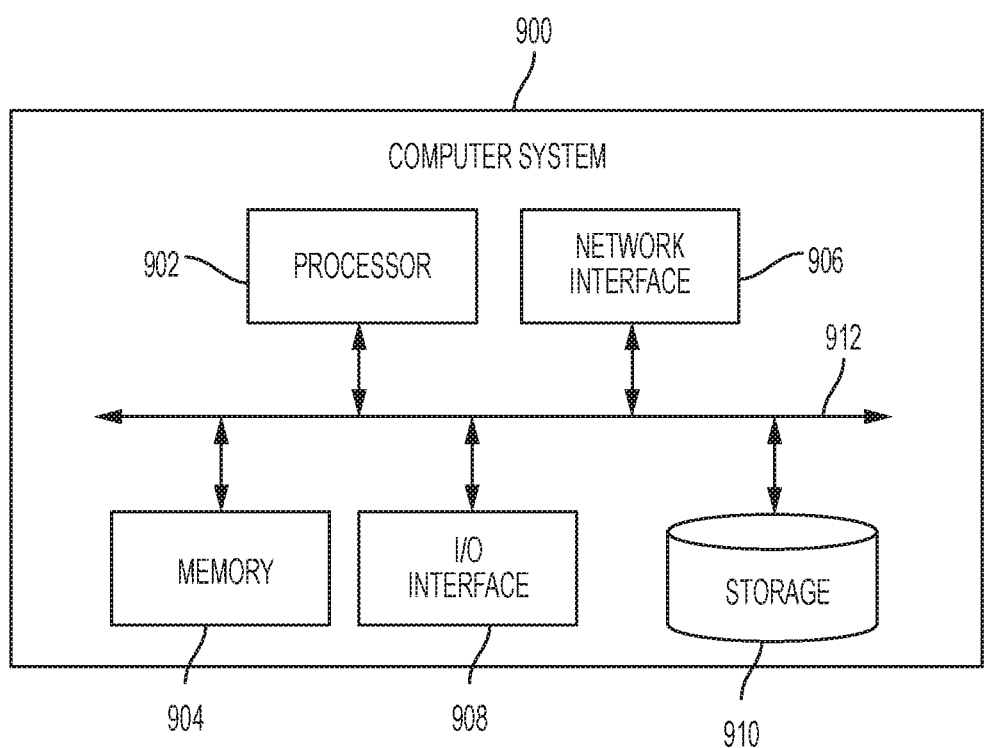
FIG. 20 illustrates one exemplary embodiment of a computer system that can be used to implement a control system of the present disclosure.

FIG. 20 illustrates one exemplary embodiment of a computer system 900. As shown, the computer system 900 includes one or more processors 902 which can control the operation of the computer system 900. "Processors" are also referred to herein as "controllers." The processor(s) 902 can include any type of microprocessor or central processing unit (CPU), including programmable general-purpose or special-purpose microprocessors and/or any one of a variety of proprietary or commercially available single or multi-processor systems. The computer system 900 can also include one or more memories 904, which can provide temporary storage for code to be executed by the processor(s) 902 or for data acquired from one or more users, storage devices, and/or databases. The memory 904 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 900 can be coupled to a bus system 912. The illustrated bus system 912 is an abstraction that represents any one or more separate physical busses, communication lines/interfaces, and/or multi-drop or point-to-point connections, connected by appropriate bridges, adapters, and/or controllers. The computer system 900 can also include one or more network interface(s) 906, one or more input/output (IO) interface(s) 908 that can include one or more interface components, and one or more storage device(s) 910.

The network interface(s) 606 can enable the computer system 900 to communicate with remote devices, e.g., motor(s) coupled to the drive system that is located within the surgical device or a robotic surgical system or other computer systems, over a network, and can be, for non-limiting example, remote desktop connection interfaces, Ethernet adapters, and/or other local area network (LAN) adapters. The IO interface(s) 908 can include one or more interface components to connect the computer system 900 with other electronic equipment, such as the sensors located on the motor(s). For non-limiting example, the IO interface(s) 908 can include high speed data ports, such as universal serial bus (USB) ports, 1394 ports, Wi-Fi, Bluetooth, etc. Additionally, the computer system 900 can be accessible to a human user, and thus the IO interface(s) 908 can include displays, speakers, keyboards, pointing devices, and/or various other video, audio, or alphanumeric interfaces. The storage device(s) 910 can include any conventional medium for storing data in a non-volatile and/or non-transient manner. The storage device(s) 910 can thus hold data and/or instructions in a persistent state, i.e., the value(s) are retained despite interruption of power to the computer system 900. The storage device(s) 910 can include one or more hard disk drives, flash drives, USB drives, optical drives, various media cards, diskettes, compact discs, and/or any combination thereof and can be directly connected to the computer system 900 or remotely connected thereto, such as over a network. In an exemplary embodiment, the storage device(s) 910 can include a tangible or non-transitory computer readable medium configured to store data, e.g., a hard disk drive, a flash drive, a USB drive, an optical drive, a media card, a diskette, a compact disc, etc.

The elements illustrated in FIG. 20 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 900 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 900 can also include a web server for generating and/or delivering the web pages to client computer systems.

In an exemplary embodiment, the computer system 900 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A surgical system, comprising:
    an electromechanical tool including an instrument shaft and an end effector with an energy-delivering electrode disposed thereon, the electrode being configured to deliver energy to tissue;
    an electromechanical arm configured for movement with respect to multiple axes, wherein the electromechanical tool is configured to be mounted on the electromechanical arm; and
    a control system operably coupled to the electromechanical arm and the electromechanical tool for controlling movement thereof, the control system being configured to determine a zone of avoidance surrounding the electromechanical tool when energy is delivered to tissue through the electrode and, when entry into the zone of avoidance by a secondary electromechanical tool is determined by the control system to be imminent, the control system is configured to do at least one of reduce a power level at which energy is delivered to the tissue by the electrode and prevent the secondary electromechanical tool from entering the zone of avoidance;

wherein the zone of avoidance is dependent at least on a power level at which the electrode is energized.

2. The surgical system of claim 1, wherein the secondary electromechanical tool is configured to be mounted to the electromechanical arm or a secondary electromechanical arm and the control system is configured to be operably coupled to the secondary electromechanical tool.

3. The surgical system of claim 2, wherein, when entry into the zone of avoidance by the secondary electromechanical tool is imminent, the control system is configured to maintain the power level and redirect the secondary electromechanical tool relative away from the zone of avoidance to prevent the secondary electromechanical tool from entering the zone of avoidance.

4. The surgical instrument of claim 1, wherein the control system is configured to detect a distance of the secondary electromechanical tool relative to the zone of avoidance to determine when entry into the zone of avoidance is imminent.

5. The surgical system of claim 1, wherein at least a portion of the secondary electromechanical tool is formed of a conductive material.

6. The surgical system of claim 1, wherein, when the power level is reduced, a size of the zone of avoidance is reduced to prevent entry of the secondary electromechanical tool into the zone of avoidance and the reduced size of the zone is maintained.

7. The surgical system of claim 1, wherein the control system is configured to detect a first energy level of the secondary electromechanical tool relative to a second energy level to determine when entry into the zone of avoidance is imminent.

8. A surgical system, comprising:
an electromechanical tool including an instrument shaft and an end effector with an energy-delivering electrode disposed thereon, the electrode being configured to deliver energy to tissue;
an electromechanical arm configured for movement with respect to multiple axes, wherein the electromechanical tool is configured to be mounted on the electromechanical arm; and
a control system operably coupled to the electromechanical arm and the electromechanical tool for controlling movement thereof, the control system being configured to determine a zone of avoidance surrounding the electromechanical tool when energy is delivered to tissue through the electrode and, when entry into the zone of avoidance by a secondary electromechanical tool is determined by the control system to be imminent, the control system is configured to do at least one of reduce a power level at which energy is delivered to the tissue by the electrode and prevent the secondary electromechanical tool from entering the zone of avoidance;
wherein, when the power level is reduced, a size of the zone of avoidance is reduced to prevent entry of the secondary electromechanical tool into the zone of avoidance and the reduced size of the zone is maintained.

9. The surgical system of claim 8, wherein at least a portion of the secondary electromechanical tool is formed of a conductive material.

10. A surgical system, comprising:
an electromechanical tool including an instrument shaft and an end effector with an energy-delivering electrode disposed thereon, the electrode being configured to deliver energy to tissue;
an electromechanical arm configured for movement with respect to multiple axes, wherein the electromechanical tool is configured to be mounted on the electromechanical arm; and
a control system operably coupled to the electromechanical arm and the electromechanical tool for controlling movement thereof, the control system being configured to determine a zone of avoidance surrounding the electromechanical tool when energy is delivered to tissue through the electrode and, when entry into the zone of avoidance by a secondary electromechanical tool is determined by the control system to be imminent, the control system is configured to do at least one of reduce a power level at which energy is delivered to the tissue by the electrode and prevent the secondary electromechanical tool from entering the zone of avoidance;
wherein the control system is configured to detect a first energy level of the secondary electromechanical tool relative to a second energy level to determine when entry into the zone of avoidance is imminent.

11. The surgical system of claim 10, wherein at least a portion of the secondary electromechanical tool is formed of a conductive material.

12. A method for operating a surgical system, comprising:
actuating an electromechanical arm to position an electromechanical tool mounted thereon for insertion into tissue, the electromechanical tool having an instrument shaft and an end effector that includes an energy-delivering electrode disposed thereon and configured to deliver energy to the tissue;
inserting at least the end effector into the tissue; and
determining, through a control system operably coupled to the electromechanical arm and the electromechanical tool, a zone of avoidance surrounding the electromechanical tool when energy is delivered to tissue through the electrode,
wherein when the control system determines that entry into the zone of avoidance by a secondary electromechanical tool is imminent, the control system reduces a power level at which energy is delivered to the tissue by the electrode or prevents the secondary electromechanical tool from entering the zone of avoidance;
wherein the zone of avoidance is dependent at least on a power level at which the electrode is energized.

13. The method of claim 12, further comprising, when entry of the secondary electromechanical tool into the zone of avoidance is imminent, redirecting, through the control system being operably coupled to the secondary electromechanical tool, the secondary electromechanical tool away from the zone of avoidance.

14. The method of claim 12, further comprising detecting, through the control system, a distance of the secondary electromechanical tool relative to the zone of avoidance to determine when entry into the zone of avoidance is imminent.

15. The method of claim 12, wherein at least a portion of the secondary electromechanical tool is formed of a conductive material.

16. A method for operating a surgical system, comprising:
actuating an electromechanical arm to position an electromechanical tool mounted thereon for insertion into tissue, the electromechanical tool having an instrument shaft and an end effector that includes an energy-delivering electrode disposed thereon and configured to deliver energy to the tissue;

inserting at least the end effector into the tissue;

determining, through a control system operably coupled to the electromechanical arm and the electromechanical tool, a zone of avoidance surrounding the electromechanical tool when energy is delivered to tissue through the electrode;

determining, through the control system, when entry into the zone of avoidance by a secondary electromechanical tool is imminent; and reducing, through the control system, a power level at which energy is delivered to the tissue by the electrode to thereby reduce a size of the zone of avoidance to prevent entry of the secondary electromechanical tool into the zone of avoidance.

17. The method of claim 16, further comprising detecting, through the control system, a first energy of the secondary electromechanical tool relative to a second energy to determine when entry into the zone of avoidance is imminent.

18. The method of claim 16, further comprising detecting, through the control system, a distance of the secondary electromechanical tool relative to the zone of avoidance to determine when entry into the zone of avoidance is imminent.

19. A method for operating a surgical system, comprising:

actuating an electromechanical arm to position an electromechanical tool mounted thereon for insertion into tissue, the electromechanical tool having an instrument shaft and an end effector that includes an energy-delivering electrode disposed thereon and configured to deliver energy to the tissue;

inserting at least the end effector into the tissue;

determining, through a control system operably coupled to the electromechanical arm and the electromechanical tool, a zone of avoidance surrounding the electromechanical tool when energy is delivered to tissue through the electrode; and detecting, through the control system, a first energy of the secondary electromechanical tool relative to a second energy to determine when entry into the zone of avoidance is imminent;

wherein when the control system determines that entry into the zone of avoidance by a secondary electromechanical tool is imminent, the control system reduces a power level at which energy is delivered to the tissue by the electrode or prevents the secondary electromechanical tool from entering the zone of avoidance.

20. The method of claim 19, further comprising, when entry of the secondary electromechanical tool into the zone of avoidance is imminent, redirecting, through the control system being operably coupled to the secondary electromechanical tool, the secondary electromechanical tool away from the zone of avoidance.

* * * * *

UNITED STATES PATENT AND TRADEMARK OFFICE
CERTIFICATE OF CORRECTION

PATENT NO. : 10,835,310 B2
APPLICATION NO. : 15/689628
DATED : November 17, 2020
INVENTOR(S) : Shelton, IV et al.

Page 1 of 1

It is certified that error appears in the above-identified patent and that said Letters Patent is hereby corrected as shown below:

On the Title Page

Item (12) should read:
Frederick E. Shelton, IV
David C. Yates
Mark A. Davison

Item (72) Inventors reads:
Frederick E. Shelton, IV
Jason L. Harris

Should read:
Frederick E. Shelton, IV
David C. Yates
Mark A. Davison

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*